US008211690B2

(12) United States Patent
Di Rago et al.

(10) Patent No.: US 8,211,690 B2

(45) Date of Patent: Jul. 3, 2012

(54) **MODELLING IN YEAST OF THE MITOCHONDRIAL *ATP6* GENE MUTATIONS RESPONSIBLE FOR NARP SYNDROME IN HUMANS AND USES THEREOF FOR SCREENING FOR MEDICAMENTS**

(75) Inventors: Jean-Paul Di Rago, Sainte-Helene (FR); Malgorzata Rak, Checiny (PL); Roza Kucharczyk, Warsaw (PL); Emmanuel Tetaud, Pessac (FR); Stephane Duvezin-Caubet, Mimbaste (FR)

(73) Assignees: Universite Victor Segalen Bordeaux 2, Bordeaux (FR); Centre National de la Recherche Scientifique, Paris (FR)

( * ) Notice: Subject to any disclaimer, the term of this patent is extended or adjusted under 35 U.S.C. 154(b) by 169 days.

(21) Appl. No.: 12/299,361

(22) PCT Filed: May 3, 2007

(86) PCT No.: PCT/FR2007/000757

§ 371 (c)(1), (2), (4) Date: Jan. 26, 2009

(87) PCT Pub. No.: WO2007/125225

PCT Pub. Date: Nov. 8, 2007

(65) Prior Publication Data

US 2010/0021955 A1 Jan. 28, 2010

(30) Foreign Application Priority Data

May 3, 2006 (FR) ..................................... 06 03934

(51) Int. Cl.
*C12N 1/00* (2006.01)
*C12N 15/70* (2006.01)

(52) U.S. Cl. .................................... 435/255.1; 435/471

(58) Field of Classification Search ........................ None
See application file for complete search history.

(56) References Cited

OTHER PUBLICATIONS

Bongorno, et al., "Developing a Mouse Model of the Mitochondria! NARP Syndrome Using AAV-Ribozymes for ATP6", Molecular Therapy, vol. 9, pp. 167, XP004634803, (2004).

Schon, E. et al., "Pathogenesis of primary defects in mitochondrial ATP synthesis", Cell & Developmental Biology, vol. 12, No. 6, pp. 441-448, XP002403535, (2001).

Holt, I.J. et al., "A New Mitochondrial Disease Associated with Mitochondrial DNA Heteroplasmy", American Journal of Human Genetics, vol. 46, No. 3, pp. 428-433, XP009073979, (1990).

Celotto, A. et al., "Mitochondrial Encephalomyopathy in Drosophila", Journal of Neuroscience, vol. 26, No. 3, pp. 810-820, XP002403537, (2006).

John, U. P. et al., "Sequence of the mitochondrial oli2 gene coding for subunit 6 of the mitochondrial ATPase complex in different strains of Saccharomyces", Nucleic Acids Research, vol. 15, No. 1, pp. 366, XP000971250, (1987).

Guelin, E. et al., "Isolation of the ATP synthase subunit 6 and sequence of the mitochondrial ATP6 gene of the yeast *Candida parapsilosis*", European Journal of Biochemistry, vol. 197, No. 1, pp. 105-111, XP002403538.

*Primary Examiner* — Michele K Joike

(74) *Attorney, Agent, or Firm* — Oblon, Spivak, McClelland, Maier & Neustadt, L.L.P.

(57) ABSTRACT

Modified yeast cells comprising at least one mutation of the tryptophan 136 ($W_{136}$), leucine 183 ($L_{183}$), or leucine 247 ($L_{247}$) codon of the mitochondrial ATP6 gene, responsible for NARP syndrome in humans and uses thereof for screening for medicaments that act against mitochondrial pathologies involving a deficiency in ATP production via the oxidative phosphorylation pathway, such as NARP syndrome.

16 Claims, 13 Drawing Sheets

Figure 1:
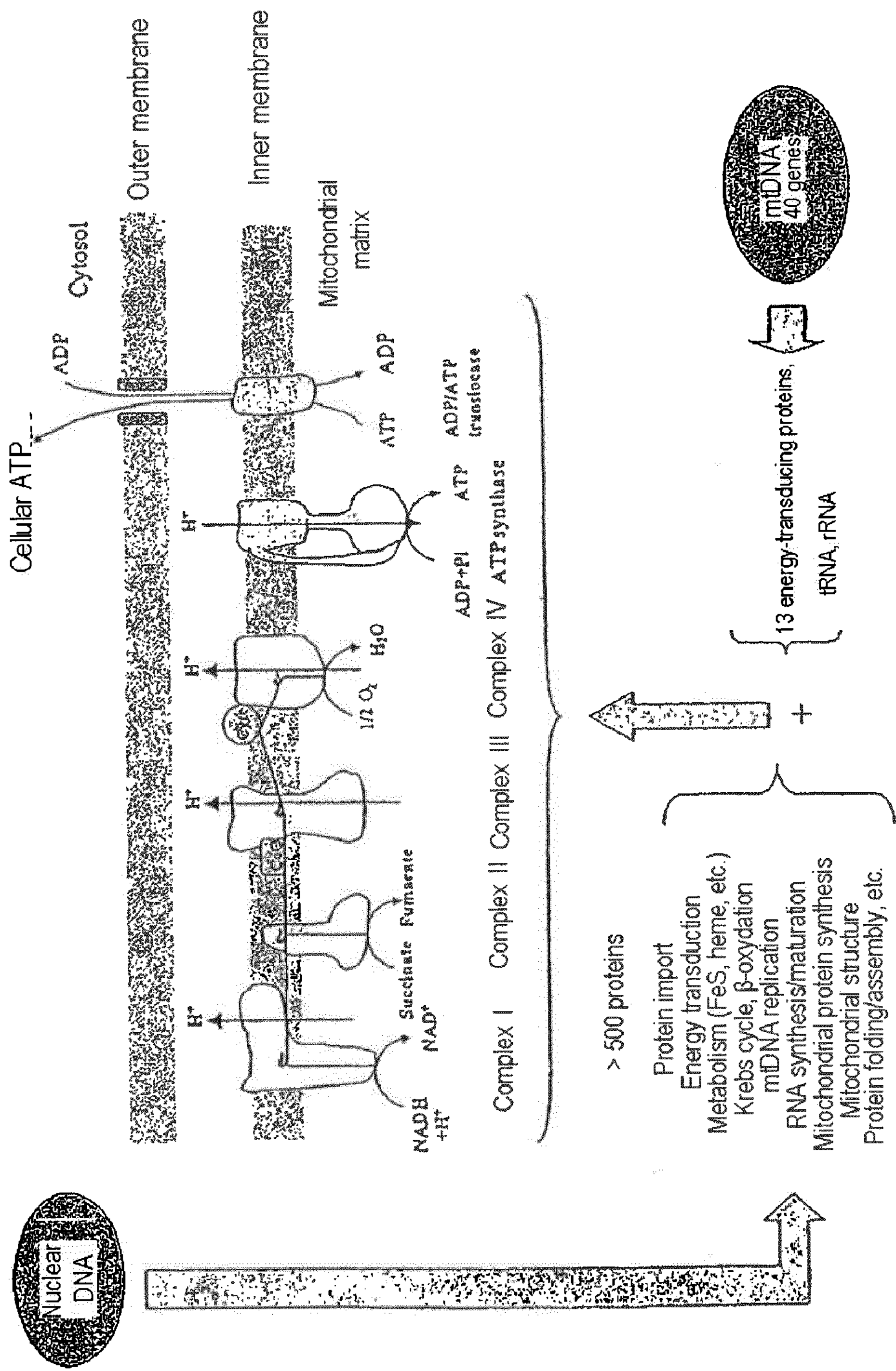

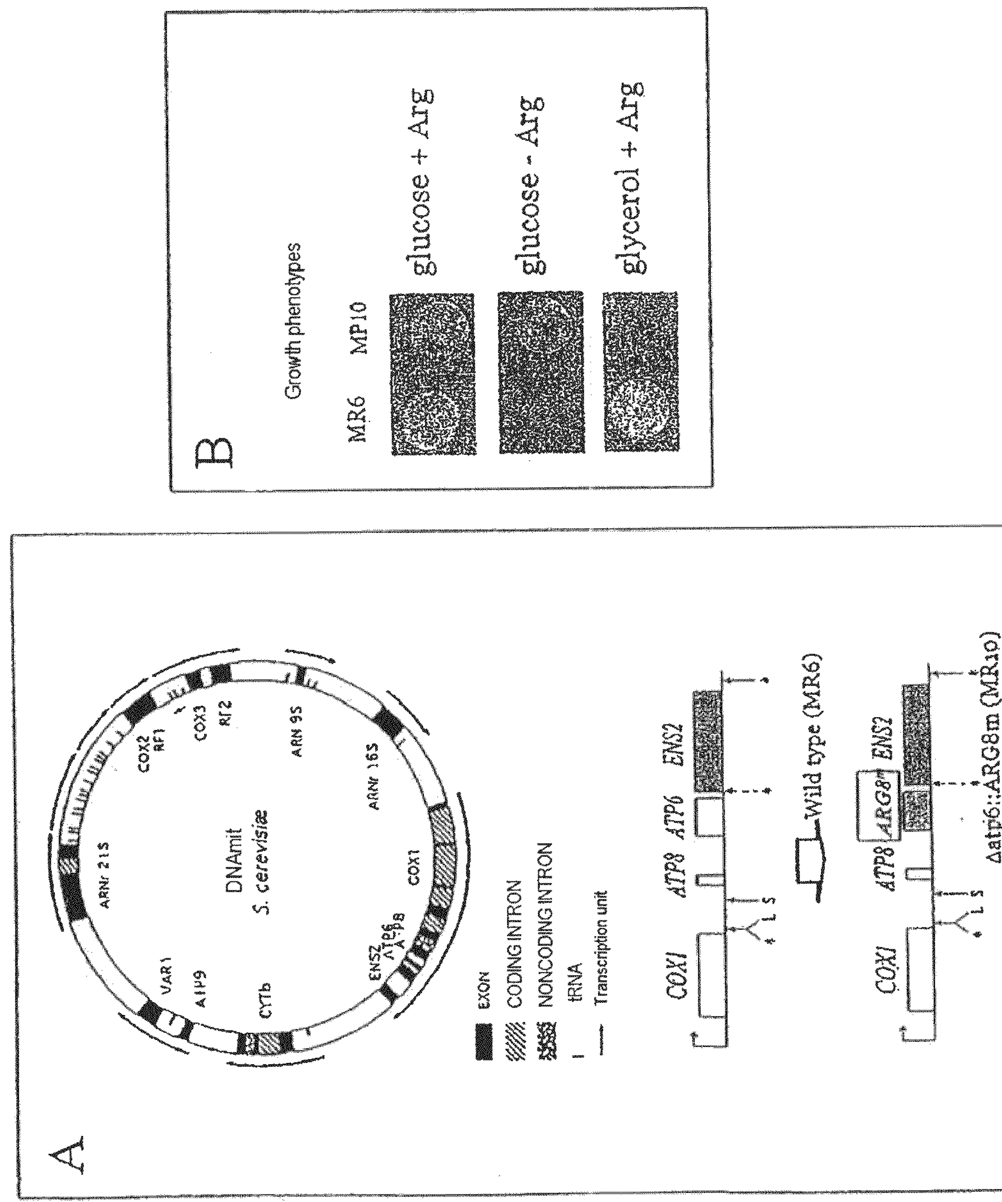
Figure 3(A&B)

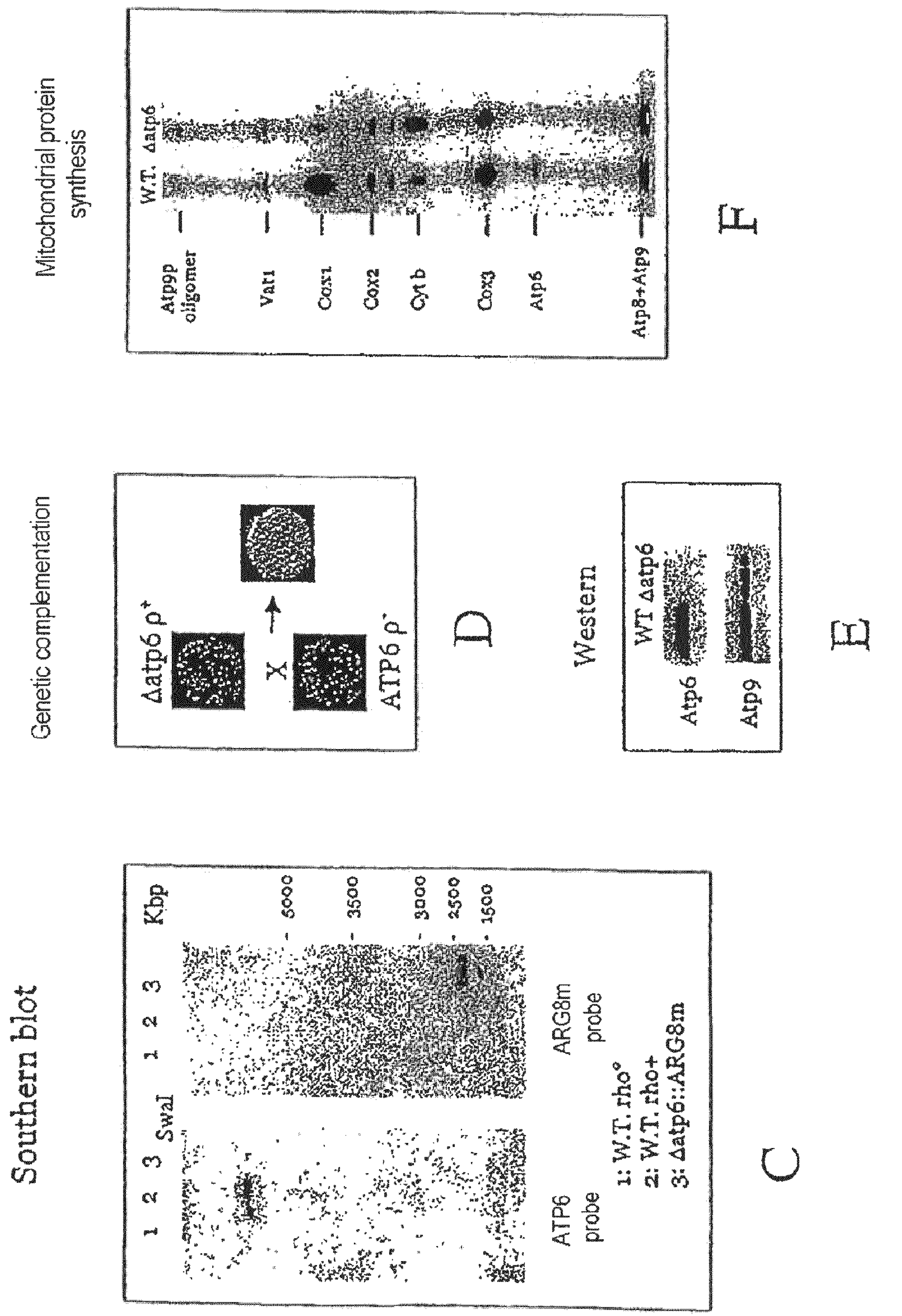
Figure 3 (C to F)

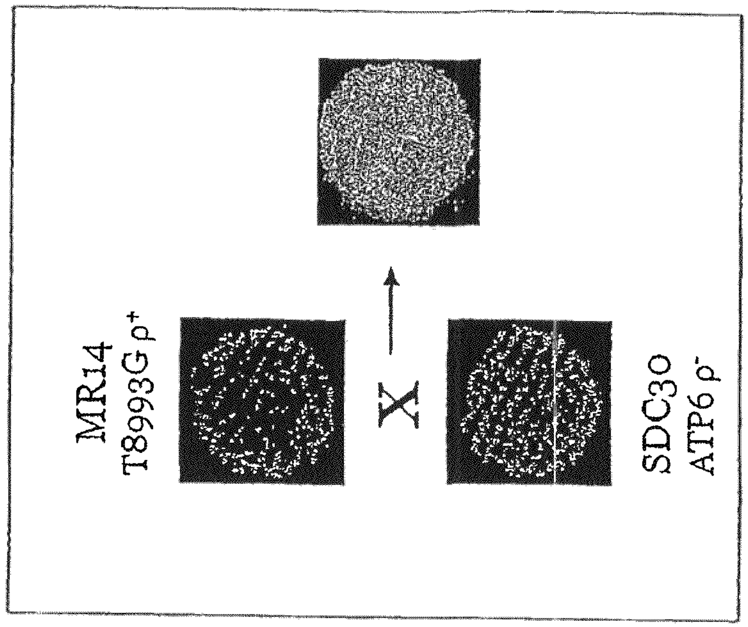
Complementation by crossing of the T8993G mutant
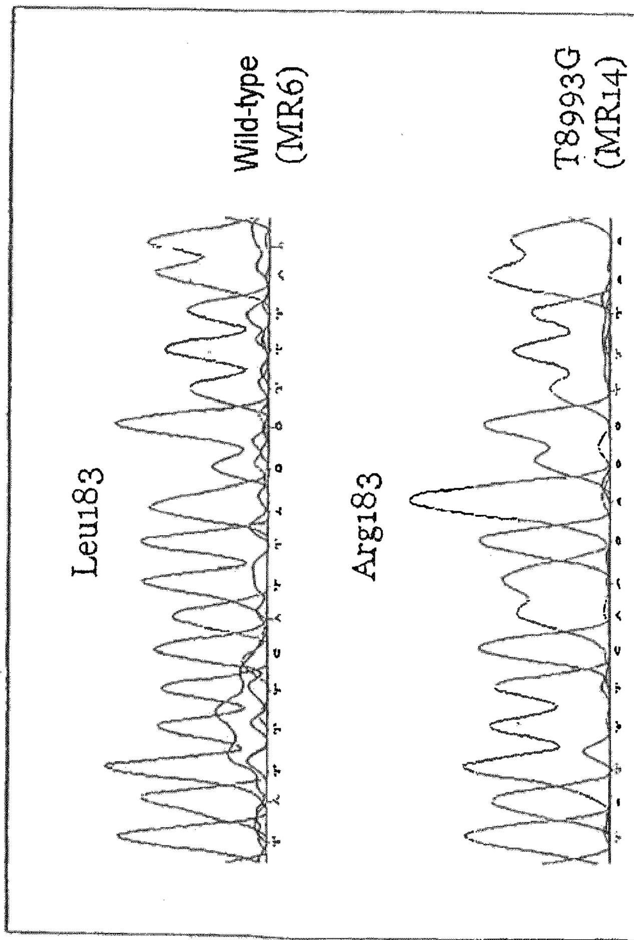
DNA sequencing
Figure 5

| Strain | % $\rho^-/\rho^\circ$ | Oxygen consumption rate (nAt/min/mg) | | | | | ATP synthesis (pmol/min/mg) | |
|---|---|---|---|---|---|---|---|---|
| | | NADH | | | | Asc/TMPD | | |
| | | RCR | State 4 | State 3 | +CCCP | +CCCP | -oligo | +oligo |
| MR6 | 2 | 2.2 ± 0.15 | 298 ± 11 | 647 ± 30 | 1231 ± 145 | 1911 ± 246 | 911 ± 106 | 174 ± 45 |
| MR14 | 7.5 | N | N | 139 ± 13 | 281 ± 24 | 430 ± 18 | 59 ± 6 | 0 ± 7 |

Figure 7

First-site reversions

| Codon change | Amino acid change | Number of clones |
| --- | --- | --- |
| $AGA_{183}$>ATA | $R_{183}$>I | 12 |
| $AGA_{183}$>AAA | $R_{183}K$ | 3 |
| $AGA_{183}$>AGC | $R_{183}S$ | 1 |

Second-site reversions

| Codon change | Amino acid change | Number of clones |
| --- | --- | --- |
| $AGA_{179}$>AGT | $R_{179}$>S | 3 |
| $GCT_{180}$>CCT | $A_{180}$>P | 1 |
| $GCT_{180}$>GGT | $A_{180}$>G | 1 |
| $ATC_{226}$>AGC | $I_{226}$>S | 1 |

MODELLING IN YEAST OF THE MITOCHONDRIAL *ATP6* GENE MUTATIONS RESPONSIBLE FOR NARP SYNDROME IN HUMANS AND USES THEREOF FOR SCREENING FOR MEDICAMENTS

CROSS-REFERENCE TO RELATED APPLICATIONS

The present application is a 35 U.S.C. §371 National Stage patent application of International patent application PCT/FR2007/000757, filed on May 3, 2007, which claims priority to French patent application FR 0603934, filed on May 3, 2006.

The present invention relates to yeast strains carrying the equivalent of mitochondrial ATP6 gene mutations responsible for NARP syndrome in humans and to the uses thereof for screening for medicaments that act against mitochondrial pathologies involving a deficiency in ATP production via the oxidative phosphorylation pathway, such as NARP syndrome.

NARP (Neuropathy, Ataxia and Retinitis Pigmentosa) is a maternally transmitted hereditary syndrome characterized by retarded development, and accompanied by retinitis pigmentosa (RP), dementia, ataxia, proximal neurological muscle weakness and sensory neuropathies (Schon et al., J. Bioenerg. Biomembr., 1994, 26, 291-299; Graeber, M. B. and Müller, U., J. Neurol. Sci., 1998, 153, 251-263, for review). This disease is in general a pathology which occurs in children, but it has also been reported in rarer cases in adults. The clinical manifestations are varied and can take more or less severe forms. Thus, the ophthalmic manifestations can range from a simple "salt and pepper" changing of the retina to severe RP, accompanied by maculopathy. Similarly, there is a broad spectrum of neurological manifestations, which ranges from simple migraines to severe dementia and to "Leigh's disease" (subacute necrotising encephalomyelopathy; Ortiz et al., Arch., Ophtalmol., 1993, 111, 1525-1530). Many retinitis pigmentosa-related syndromes exist, such as Usher's syndrome in which both the sight and the hearing are affected, or else macular dystrophy, also called inverse RP.

In 1990, Holt et al. (Am. J. Hum. Genet., 46, 428-433) described for the first time the presence of the t8993g mutation (or T8993G) in the mitochondrial DNA of patients showing NARP syndrome/Leigh's disease. It was subsequently postulated by Tatuch and Robinson (Biochem. Biophys. Res. Commun., 1993, 192, 124-128) that this mutation resulted in a reduction in ATP synthesis by impairing the mitochondrial ATP synthase complex. This mutation is thought to be responsible for an ATP synthase assembly/stability defect (Nijtmans et al., J. Biol. Chem., 2001, 276, 6755-6762). Other ATP6 gene mutations have also been detected, in association with NARP syndrome/Leigh's disease; t8993c, t9176g, t9176c and t8851c (Schon et al., Cell & Dev. Biol., 2001, 12, 441-448). A simple point mutation is therefore responsible for this syndrome, which has many more or less serious forms. The great diversity of the pathological manifestations is attributed to the heteroplasmic nature of this mutation in patients, i.e. the coexistence of mutated and wild-type mitochondrial DNA molecules in the cells or tissues. The mutated mitochondrial DNA load is closely correlated with the seriousness of the symptoms observed (Uziel et al., J. Neurol. Neurosurg. Psychiatry, 1997, 63, 16-22; Carelli et al., Arch. Neurol., 2002, 59, 264-270). For example, Leigh's encephalopathy is observed when the proportion of mutated mitochondrial DNA is very high (>90-95%). When the mutation is present in a lower proportion (<75%), it results in the development of NARP syndrome (Shoffner et al., Neurology, 1992, 42, 2168-2174; Ortiz et al., Arch., Ophtalmol., 1993, 111, 1525-1530; Wallace D C, Science, 1999, 283, 1482-1488, for review; Graeber, M. B. and Müller, U., J. Neurol. Sci., 1998, 153, 251-263, for review).

Figure 2:
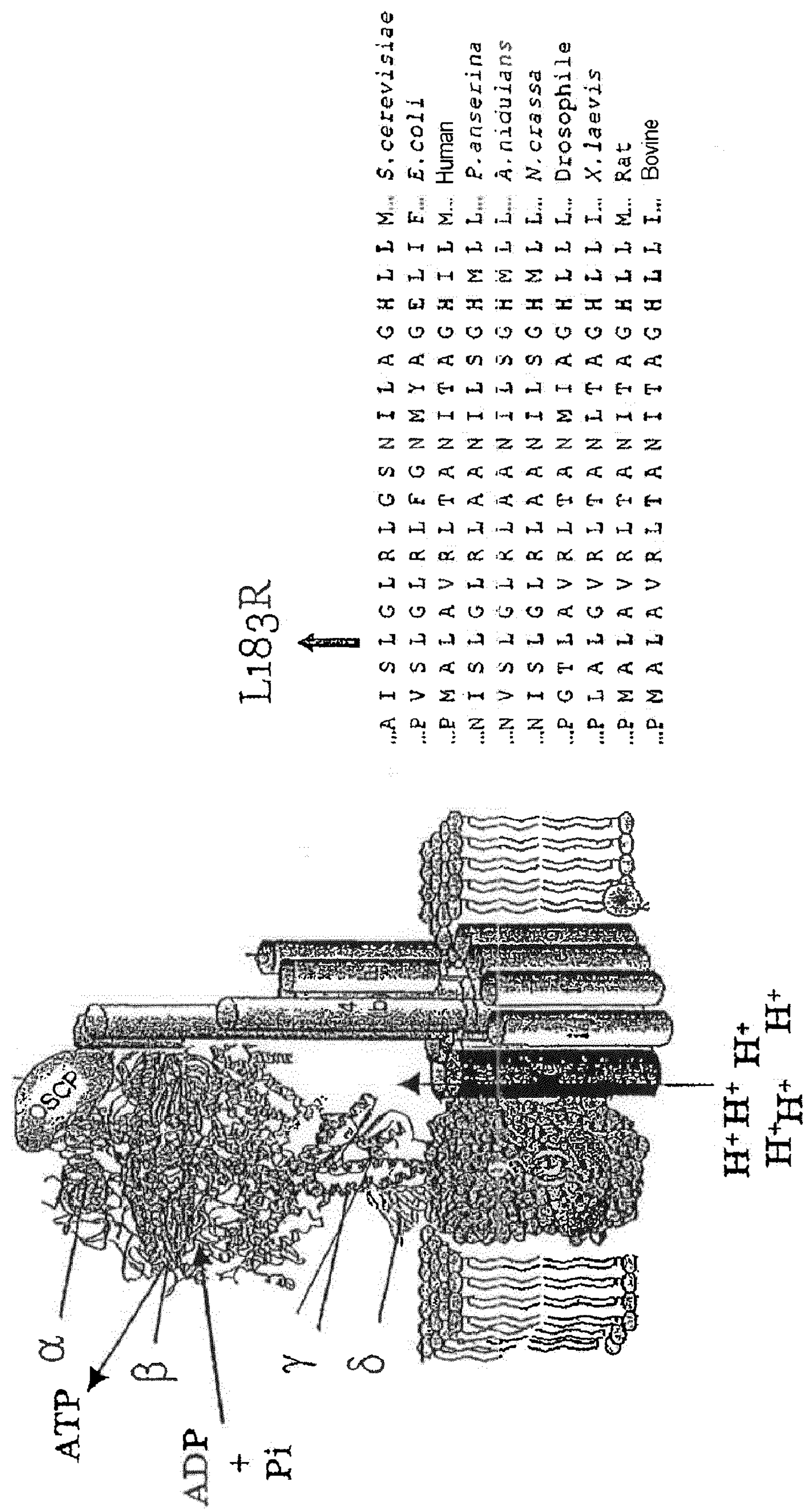

The ATP synthase complex, which is the target of the t8993g mutation, is located in the inner mitochondrial membrane (FIGS. 1 and 2). It catalyzes the last steps of oxidative phosphorylation, a process which allows cells to extract the chemical energy of metabolites and to store this energy in ATP molecules. In order to synthesize ATP, the ATP synthase complex uses the electrochemical proton gradient on either side of the inner membrane, generated by other complexes located in this membrane, the respiratory complexes (FIG. 1). The latter transfer to oxygen the reducing equivalents of the substrates that are oxidized in the mitochondrion. These transfers are coupled to proton transports (hydrogen ions, $H^+$) across the inner membrane, from the inside (the mitochondrial matrix) into the space between the outer and inner membranes (intermembrane space) of the organelle. The result is a protein concentration that is higher at the outer periphery of the inner membrane than at its inner periphery. The membrane domain ($F_o$) of ATP synthase enables a channeled return of the protons into the mitochondrial matrix. This transport is coupled to ATP synthesis in the catalytic domain $F_1$ of ATP synthase located outside the membrane, in the mitochondrial matrix. ATP synthase operates like a rotary turbine: the passage of protons in $F_o$ is coupled to the rotation of a subcomplex (the rotor) of the enzyme. This rotation results in confirmational changes in $F_1$ which promote the synthesis of ATP from ADP and from inorganic phosphate (Boyer P. D., Annu, Rev., Biochem., 1997, 66, 717-747). The neosynthesized ATP molecules can, via a specific transporter located in the inner membrane (ADP/ATP translocase), leave the mitochondrial compartment so as to supply the entire cell with energy. ATP synthase comprises about twenty different protein subunits for a mass of approximately 600 KDa. In humans, two ATP synthase subunits (Atp6p and Atp8p) are encoded by the mitochondrial genome, all the other subunits being encoded by nuclear genes. The subunits of nuclear origin are synthesized in the cytosol and then imported into the mitochondrion, whereas the Atp6p and Atp8p subunits encoded by the mitochondrial genome are actually synthesized inside the mitochondrion.

The t8993g mutation associated with NARP syndrome is located in the mitochondrial ATP6 gene. The latter encodes ATP synthase subunit 6 (Atp6p) which is essential for proton transport across $F_o$ (FIG. 2). The t8993g mutation results in the replacement, with arginine, of a leucine residue conserved in all the known sequences of Atp6p, from bacteria to humans. This leucine residue is in an Atp6p region presumed to be transmembrane and essential for ATP synthase proton translocation activity. Studies carried out in the *Escherischia coli* bacterium or with NARP cybrids (human cells in which the mitochondria are enriched, up to 100%, in t8993g alleles) indicate that the t8993g mutation clearly affects the functioning of the ATP synthase proton channel and that this defect is the primary cause of the disease (Schon et al., Cell & Dev. Biol., 2001, 12, 441-448; Nijtmans et al., J. Biol. Chem., 2001, 276, 6755-6762).

There is currently no effective medicament for the treatment of NARP syndrome, nor any cellular model for this syndrome that is suitable for massive screening for molecules of therapeutic interest.

In fact, the use of human cell-derived cybrids involves a cell culture step which is long, difficult, laborious and expensive for mammalian cells which divide slowly (doubling time of at least 24 hours), require complex culture media, are sensitive to contamination with microorganisms, and cannot be cultured on a solid (agar) medium. In addition, cybrids are relatively insensitive cells for studying NARP syndrome.

Furthermore, bacteria do not have mitochondria and, in this respect, they are not a good model for studying the impact of pathogenic mutations of the ATP6 gene on mitochondrial physiology. In addition, even though the ATP synthases of bacteria and of eucaryotic cells (mammalian, yeast cells) function similarly, they possess, however, considerable structural differences with, in particular, about ten additional or "surplus" subunits in eucaryotic ATP synthases which have no equivalent in bacteria (Velours, J. and Arselin, G., J. Bioenerg. Biomembr., 2000, 32, 383-390).

The baker's yeast *Saccharomyces cerevisiae*, a single-cell fungus, has for more than about ten years been a reference model for studying mitochondria. One decisive advantage is the good fermentative capacity of yeast, such that this organism is capable of surviving mutations which inactivate the mitochondrial energy system. It is thus possible to correctly keep alive mutants which no longer synthesize ATP via the mitochondrial pathway. In particular, yeast is a good model for isolating and studying mitochondrial DNA mutants. The yeast mitochondrial genome, as in humans, is a small circular double-stranded DNA molecule. In yeast, this genome encodes (FIG. 3) seven subunits of the mitochondrial energy system: one complex III subunit (cytochrome b), three complex IV subunits (Cox1p, Cox2p, Cox3p) and three ATP synthase subunits (Atp6p, Atp8p and Atp9p). It also contains some genes required for the mitochondrial protein synthesis system: one protein subunit (Var1) and the RNA components (15S and 21S) of the mitoribosome, and a set of 24 transfer RNAs sufficient for deciphering all the open reading frames of the mitochondrial genome. The mitochondrial genome is therefore only required for the expression of oxidative phosphorylation. This is why the yeast, by virtue of its good fermentative capacity, is capable of surviving the loss of the mitochondrial genes.

Several copies of the mitochondrial genome are present per cell, thousands in human cells, about fifty in yeast. However, although mutations of the mitochondrial genome, such as the t8993g mutation, are heteroplasmic in mammalian cells, heteroplasmy is normally unstable in yeast. As a result, in yeast, it is possible to obtain pure (homoplasmic) clones where all the mitochondrial DNA molecules carry a given mutation. This makes it possible to analyze with precision the effects of a given mutation of the mitochondrial DNA. The yeast is one of the rare organisms in which it is possible to introduce defined mutations into the mitochondrial genome by means of a biolistic method (Bonnefoy, N and Fox, T. D., Methods Cell. Biol., 2001, 65, 381-396).

Site-directed mutagenesis of mitochondrial DNA is a technique which is well mastered in yeast, and many mutations have already been introduced successfully into this DNA, in particular the COB-BOX and COX2 genes (Bonnefoy et al., Mol. Cell. Biol., 2001, 21, 2359-2372). However, up until now, it has not been possible to successfully introduce any defined mutation into the mitochondrial ATP synthase genes.

In fact, in the 1970s, deleterious point mutations of mitochondrial DNA ($mit^-$) were sought with a view to being able to better define mitochondrial genes and the laws governing their transmission (Slonimski, P. P. and Tzagoloff, A., Eur., J. Biochem., 1976, 61, 27-41). The mutants had been isolated in an op1 nuclear context. The mitochondrial genome loss mutation ($\rho^-/\rho^o$) is lethal in this context and therefore nonselectable. The advantage is to facilitate the obtaining of $mit^-$ mutations since the latter appear at much lower frequencies ($10^{-5}$ to $10^{-8}$) than the $\rho^-/\rho^o$ mutation ($10^{-2}$). Using this approach, hundreds of $mit^-$ mutants were isolated and characterized. However, none of the mutants obtained affected any of the mitochondrial ATP synthase genes (ATP6, ATP8 and ATP9). These studies provided the teaching that $mit^-$ mutations in these genes are incompatible with maintaining the mitochondrial genome. This teaching was subsequently reinforced by the fact that nuclear mutations of ATP synthase (in particular in the ATP16 and ATP3 genes) massively destabilize the mitochondrial genome with an exclusive accumulation of $\rho^-/\rho^o$ cells (Velours, J. and Arselin, G., J. Bioenerg. Biomembr., 2000, 32, 383-390).

Contrary to this well-established teaching, based on prior studies, the inventors have shown that it is possible to obtain $mit^-$ mutations, in a stable form, in the mitochondrial ATP synthase genes.

In fact, the inventors have developed a system which facilitates the obtaining of ATP6 gene mutations. Using this system, they have succeeded, for the first time, in constructing yeast strains carrying the equivalent of mitochondrial ATP6 gene mutations responsible for NARP syndrome in humans. The analyses have shown that these mutations more or less severely impair the functioning of yeast ATP synthase, as in humans; three of these mutants show very retarded growth using a nonfermentable carbon source (such as glycerol). On the other hand, these mutants grow normally in the presence of glucose, a substrate which in yeast allows efficient production of ATP by fermentation, which does not require the presence of a functional ATP synthase complex.

As a result, these yeast mutants can advantageously be used to search for medicaments capable of reducing the deleterious effects caused by the mutations associated with NARP syndrome, in particular by screening chemical libraries. These yeast mutants make it possible to identify molecules capable of correcting the effects of the mutation by restoring either ATP synthase function, or sufficient production of ATP in the mitochondria, via a pathway other than that of oxidative phosphorylation. The molecules capable of restoring ATP synthase function can potentially be used as medicaments for the treatment of NARP syndrome. The molecules capable of restoring ATP production in the mitochondria can potentially be used as medicaments for the treatment not only of NARP syndrome, but also of other mitochondrial pathologies involving a deficiency in ATP production via the oxidative phosphorylation pathway; these are in particular pathologies related to a respiratory complex dysfunction, such as the syndromes LHON (Leber's Hereditary Ootic Neuropathy), MILS (Maternally Inherited Leigh Syndrome), MERRF (Myoclonic Epilepsy with Ragged-Red Fibers) and HSP (Hereditary Spastic Paraplegia).

The drugs are selected for their ability to restore respiratory growth of the yeast mutant. Screening technology with yeast cells is well mastered and has already been successfully used to identify anti-prion molecules active both in yeast models and mammalian models (Bach et al., Nature Biotechnology, 2003, 21, 1075-1081). Such a screening with yeast is simple to carry out, rapid, relatively inexpensive and easy to automate, and tens of thousands of molecules can thus be tested in barely a few months.

Consequently, a subject of the present invention is a modified yeast cell, characterized in that it comprises a mutation of the tryptophan 136 ($W_{136}$), leucine 183 ($L_{183}$) or leucine 247 ($L_{247}$) codon of the mitochondrial ATP6 gene.

DEFINITIONS

The terms "yeast cell", "yeast strain", "cell", "yeast" and "strain" are considered to be equivalent in the context of the present invention and are used without distinction; the same is true of the yeast strains $rho^+$, $rho^0$ and $rho^-$ as defined below.

- $rho^+$ ($\rho^+$) strain: yeast strain comprising an intact and functional mitochondrial DNA as in wild-type strains.
- $rho^0$ ($\rho^0$) strain: yeast strain devoid of mitochondrial DNA, characterized by an inability to grow in a medium containing a nonfermentable carbon source and an absence of mitochondrial protein synthesis.
- Synthetic $rho^-$ ($\rho^-$) strain: yeast strain initially $rho^0$, the mitochondria of which have been transformed with an exogenous DNA (heterologous DNA), in particular by the abovementioned biolistic yeast cell bombardment method. This transformation is made possible by the ability of the yeast cells to be able to replicate and maintain any DNA fragment, in particular a bacterial vector (plasmid). As in a natural $rho^-$ strain, the DNA artificially introduced into the mitochondria will be replicated so as to produce, in the organelle, a mass of DNA equivalent to that present in $rho^+$ wild-type strain mitochondria. The gene of interest will therefore be present in the synthetic $rho^-$ strain at a relatively high copy number (more than 3000 for a gene of interest of approximately 1 kb). It is therefore because of these properties close to those of the (natural) $rho^-$ cells that such cells are by analogy referred to as synthetic $rho^-$ cells.
- $mit^-$ strain: yeast strain comprising a local alteration (nucleotide substitution, short deletion or insertion) in the sequence of a mitochondrial gene which encodes one of the subunits of the mitochondrial energy system.
- Mitochondrial transformants: transformants obtained in particular by bombardment of yeast cells, according to the abovementioned biolistic method. The bombardment of a $rho^0$ strain results in the production of mitochondrial transformants which are synthetic $rho^-$ transformants. Any vector can be used for the bombardments, but in order to identify the mitochondrial transformants, a vector comprising a yeast mitochondrial genome marker, for example the COX2 gene, or a fragment of said gene, is necessary.
- Mitochondrial recombinants: they are obtained by homologous recombination after bringing the synthetic $rho^-$ strain into contact with a $rho^+$ strain.
- Molecule library or chemical library: a collection of molecules, related in terms of their structure, their origin or their function, in particular a combinatorial library including molecules which differ from one another by the systematic or random replacement of their elementary constituents, for example a library of oligomers such as peptides, oligonucleotides (aptamers) and oligosaccharides, or else a library of organic molecules other than oligomers, which may be cyclic or noncyclic, in particular small organic molecules, i.e. of molecular mass less than 2500 Da, preferably less than 2000 Da, preferably less than 1500 Da, more preferably less than 1000 Da, even more preferably less than 750 Da.
- ATP6 gene: the gene corresponding to positions 28487 to 29266 in the mitochondrial genome of *Saccharomyces cerevisiae* (NCBI accession number NC_001224.1) or the sequence SEQ ID NO: 1 in the sequence listing attached in the annex. Codon 136 (positions 406-408 of the nucleotide sequence SEQ ID NO: 1) is tga, which specifies a tryptophan (W) residue. Codon 183 (positions 547-549 of the nucleotide sequence SEQ ID NO: 1) is tta, which specifies a leucine (L) residue. Codon 247 (positions 739-741 of the nucleotide sequence SEQ ID NO: 1) is tta, which specifies a leucine (L) residue.
- Atp6p: the protein encoded by the ATP6 gene. The sequence of Atp6p of the *S. cerevisiae* yeast has the Swiss-Prot accession number P00854 and corresponds to the SEQ ID NO: 2 in the sequence listing attached in the annex; the amino acid at position 136 is a tryptophan (W) residue, and the amino acids at positions 183 and 247 are leucine (L) residues.
- Mutation of a codon: the substitution or the deletion of one or more nucleotides of a codon, and also the insertion of a nucleotide sequence into a codon.

In accordance with the invention, the ATP6 gene mutation is a deleterious mutation, i.e. a mutation which impairs the activity of the Atp6p ATP synthase. This impairment can be evaluated, in vitro or in vivo, by any technique known to those skilled in the art. Among the techniques in vitro (using isolated mitochondria), mention may in particular be made of: measurement of ATP synthesis by the ATP synthase complex, analysis of the mitochondrial electrical potential, and measurement of the rate of oxygen consumption by mitochondria, in the presence of NADH as respiratory substrate. Among the techniques in vivo, mention may in particular be made of analysis of respiratory growth of yeasts, i.e. growth in the presence of a nonfermentable carbon source.

According to one advantageous embodiment of said cell, said mutation is a substitution of the tryptophan or leucine codon with an arginine or proline codon, preferably an arginine codon, preferably an aga codon.

Said mutation is preferably selected from the group consisting of: W136R, L183R and L247R.

According to another advantageous embodiment of said cell, it derives from a $rho^+$ strain of *Saccaromyces cerevisiae*, such as, in particular, the strain W303-1B (MAT$\alpha$, leu2-3, leu2-112, trp1-1, ura3-1, his3-11, his3-15, ade2-1, can1-100; ATCC #201238).

The yeast strain according to the invention may be produced by crossing a mitochondrial transformant (synthetic $rho^-$ strain) containing only the mutated ATP6 gene in its mitochondria, with a wild-type strain ($rho^+$ strain containing a wild-type mitochondrial genome including the wild-type ATP6 gene), and isolating the haploid recombinants (cytoductants) containing a mutated mitochondrial genome including the mutation of codon 136, 183 or 247 of the ATP6 gene.

Alternatively, the yeast strain may be produced in two steps, in order to facilitate isolation of the mutants. In a first step, the mitochondrial ATP6 gene is deleted and replaced with a genetic marker independent of respiratory function, such as in particular $ARG8^m$; this step is carried out by crossing a mitochondrial transformant (synthetic $rho^-$ strain) containing an ATP6 gene inactivation cassette in its mitochondria, with a wild-type strain, and isolating the haploid recombinants (cytoductants) containing a mutated mitochondrial genome in which the ATP6 gene is replaced with the genetic marker. In a second step, the recombinant obtained in the first step is crossed with a mitochondrial transformant (synthetic $rho^-$ strain) containing only the mutated ATP6 gene in its mitochondria. The haploid recombinants (cytoductants) contain a mutated mitochondrial genome in which the genetic marker is replaced with an ATP6 gene mutated at codon 136, 183 or 247.

The nucleic acids are manipulated according to conventional molecular biology methods, using the standard protocols as described in: *Current Protocols in Molecular Biology* (Frederick M. AUSUBEL, 2000, Wiley and son Inc, Library of Congress, USA) and *Molecular Cloning: A Laboratory*

*Manual, Third Edition* (Sambrook et al., 2001. Cold Spring Harbor, N.Y.: Cold Spring Harbor Laboratory press).

The transformation of the mitochondria and the mitochondrial genome manipulations are carried out according to the conventional techniques as described in Bonnefoy N and Fox T. D., Mol. Gen. Genet., 2000, 262, 1036-1046 and Methods Cell. Biol., 2001, 65, 381-396.

A subject of the present invention is also the use of a modified yeast cell as defined above, the screening for medicaments that act against mitochondrial pathologies involving a deficiency in ATP production via the oxidative phosphorylation pathway.

These pathologies are related to a dysfunction of the mitochondrial energy system, such as, in particular, NARP syndrome, related to an ATP synthase dysfunction, and the syndromes LHON (Leber's Hereditary Ootic Neuropathy), MILS (Maternally Inherited Leigh Syndrome), MERRF (Myoclonic Epilepsy with Ragged-Red Fibers) and HSP (Hereditary Spastic Paraplegia), related to a respiratory complex dysfunction.

A subject of the present invention is also a method for screening for medicaments that act against mitochondrial pathologies involving a deficiency in ATP production via the oxidative phosphorylation pathway, characterized in that it comprises:

a) culturing a modified yeast cell, as defined above, in the presence of a test molecule, in a medium containing a nonfermentable carbon source, and b) identifying the molecules capable of restoring the growth of said modified yeast cells.

In the mutant yeast strains, in particular the L183R, L247R and W136R mutants, the ATP synthase dysfunction is reflected by a very retarded growth using a nonfermentable carbon source such as glycerol. Consequently, these yeast mutants make it possible to identify molecules capable of reducing the deleterious effects caused by the mutation; the screening is performed on restoration of the growth of the mutant in culture medium containing a nonfermentable carbon source.

In accordance with the invention, the culture medium is liquid or solid. Preferably, it is a solid medium such as an agar medium. When the culture medium is liquid, the test molecule is added to the medium. When the culture medium is solid, the yeasts are inoculated at the surface of the medium and the test molecule is brought into contact with the yeast, in particular by application of the test molecule to the yeast, for example by means of a filter (porous membrane) containing the test molecule. The culture is carried out under conditions which allow the growth of the corresponding nonmodified yeasts (yeast into which the mutations were introduced). The restoration of the growth of the yeast is measured by any suitable technique known to those skilled in the art, such as in particular spectrometry (measurement of the optical density of the culture, in the case of a liquid culture medium) or visualization of a growth halo at the surface of the culture medium (agar culture medium).

According to one advantageous embodiment of said method, said mitochondrial pathology is a syndrome selected from the group consisting of: NARP, LHON (Leber's Hereditary Ootic Neuropathy), MILS (Maternally Inherited Leigh Syndrome), MERRF (Myoclonic Epilepsy with Ragged-Red Fibers) and HSP (Hereditary Spastic Paraplegia).

According to another advantageous embodiment of said method, the bringing into contact in step a) is carried out by applying a filter, containing the test molecules, to a solid medium (agar medium) inoculated with said modified yeasts.

Figure 10:
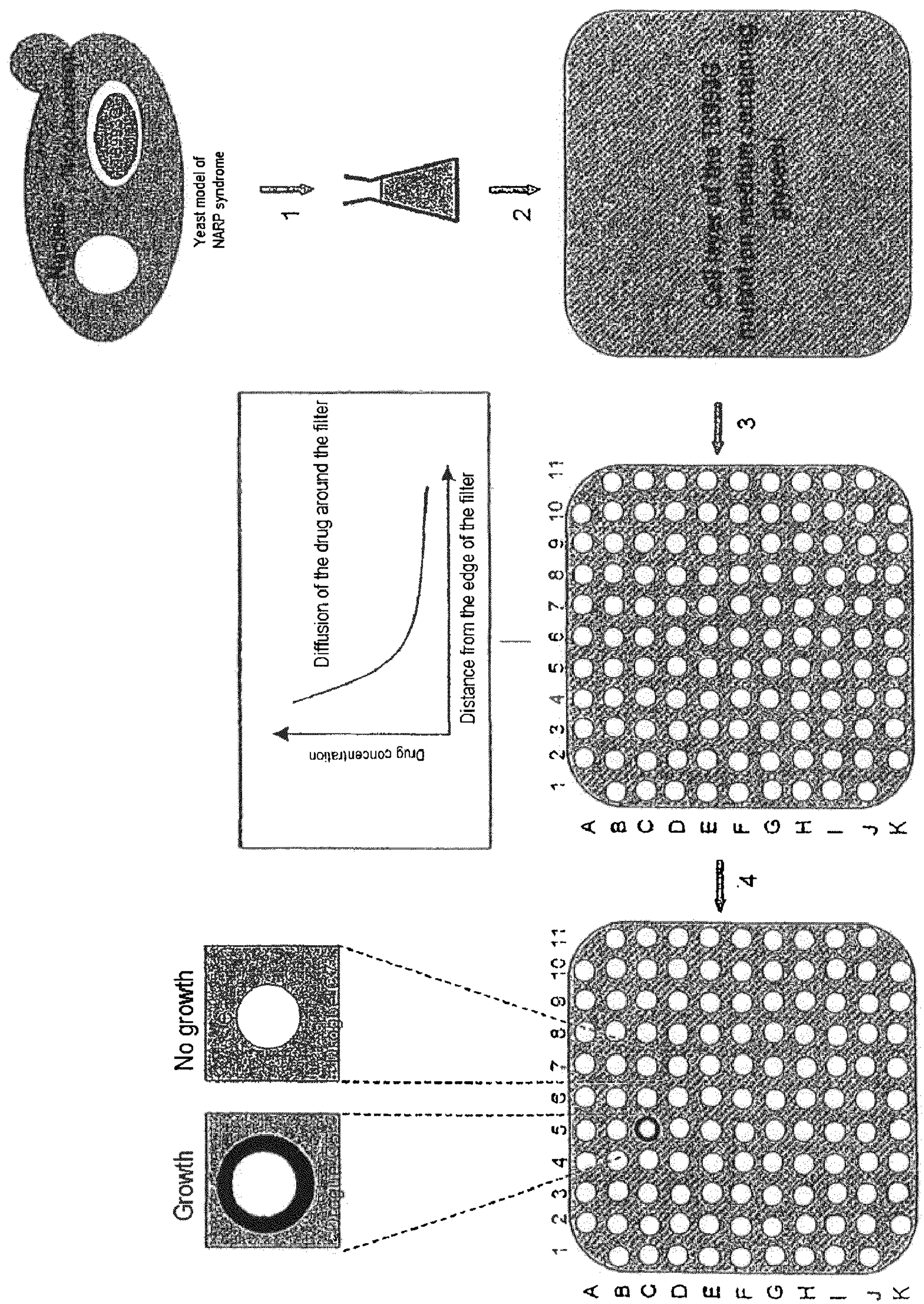

For example, a screening test according to the principle described in Bach et al., mentioned above, can be envisioned. For this, a layer of the cells of the mutant can be plated out at the surface of an agar medium containing a nonfermentable carbon source (glycerol). Filters which each contain a given amount of a molecule are subsequently placed on the cell layer in an ordered manner. The drugs diffuse in the culture medium and a concentration gradient is set up around the filters. If a molecule makes it possible to counteract the effects of the mutation, this will result in a growth halo around the filter (FIG. 10). Such a screening with the yeast is very simple to carry out and tens of thousands of molecules can thus be tested in barely a few months.

According to another advantageous embodiment of said method, said nonfermentable carbon source is selected from the group consisting of glycerol, ethanol and lactate. These compounds are used at final concentrations in the culture medium of the order of 20 g/l for the glycerol and the lactate and 30 ml/l for the ethanol.

Among the types of test molecule, mention may in particular be made of:

small molecules capable of binding specifically to ATP synthase, in the vicinity of the Atp6p region modified by the mutation, and of restoring ATP synthase functions. In fact, discrete changes in the Atp6p protein make it possible to compensate for the presence of the mutation. Consequently, such molecules could restore ATP synthase function by inducing a discrete conformational change making it possible to relax the constraint caused by the mutation. In the case of the L183R mutation, the residues in the vicinity of the mutation that can be targeted by these molecules comprise the amino acids at positions 179, 180, 183 and 226. These molecules capable of restoring ATP synthase function can potentially be used as a medicament for the treatment of NARP syndrome;

metabolic suppressors of the mutation, i.e. molecules capable of correcting the deficiency in ATP synthesis via the oxidative phosphorylation pathway, caused by the dysfunction of the mitochondrial ATP synthase complex, in particular molecules capable of stimulating alternative pathways for ATP synthesis in the mitochondria. In fact, the overexpression, in the mutant yeast strain t8993g, of Odc1p, an inner membrane protein which transports $\alpha$-ketoglutarate in the mitochondrion, results in an increased production of ATP in the mitochondria via substrate-level ADP phosphorylation, in the Krebs cycle. Thus, the molecules which result in a disturbance of Odc1p expression could increase intramitochondrial ATP production in the Krebs cycle and thus compensate for the ATP synthase dysfunction caused by the t8993g mutation. These molecules capable of restoring ATP production by mitochondria can potentially be used as a medicament for the treatment not only of NARP syndrome, but also of other mitochondrial pathologies, related in particular to a respiratory complex dysfunction, such as the syndromes LHON (Leber's Hereditary Ootic Neuropathy), MILS (Maternally Inherited Leigh Syndrome), MERRF (Myoclonic Epilepsy with Ragged-Red Fibers) and HSP (Hereditary Spastic Paraplegia).

In addition to the above provisions, the invention also comprises other provisions which will become clear from the description which follows, which refers to examples illustrating the construction, the genetic and molecular characterization and the use of mutant yeast strains carrying the equivalent of mitochondrial ATP6 gene mutations responsible for NARP syndrome in humans, and also to the attached drawings in which:

FIG. 1 is a schematic representation of the mitochondrial energy transduction apparatus and of the genes controlling the formation thereof;

FIG. 2 illustrates the structure of the ATP synthase and of the t8993g mutation associated with NARP syndrome. A. Structure of ATP synthase: the Atp6p subunit is part of the $F_o$ sector of ATP synthase; the Atp6p/Atp9p assembly constitutes the proton channel. B. Mutation associated with NARP syndrome: the t8993g mutation associated with NARP syndrome results in the replacement of a conserved leucine residue of the Atp6p subunit, with arginine (at position 156 in humans; 183 in yeast). In the structural models, this leucine residue is located in the inner membrane at the interface between the Atp6p subunit and the ring of Atp9p subunits; FIG. 2 discloses SEQ ID NOS: 7-16, respectively, in order of appearance.

FIG. 3 illustrates the construction and the genetic and molecular analysis of the MR10 mutant comprising the deletion of the mitochondrial ATP6 gene and the replacement of this gene with the ARG8$^m$ genetic marker.

Figure 4:
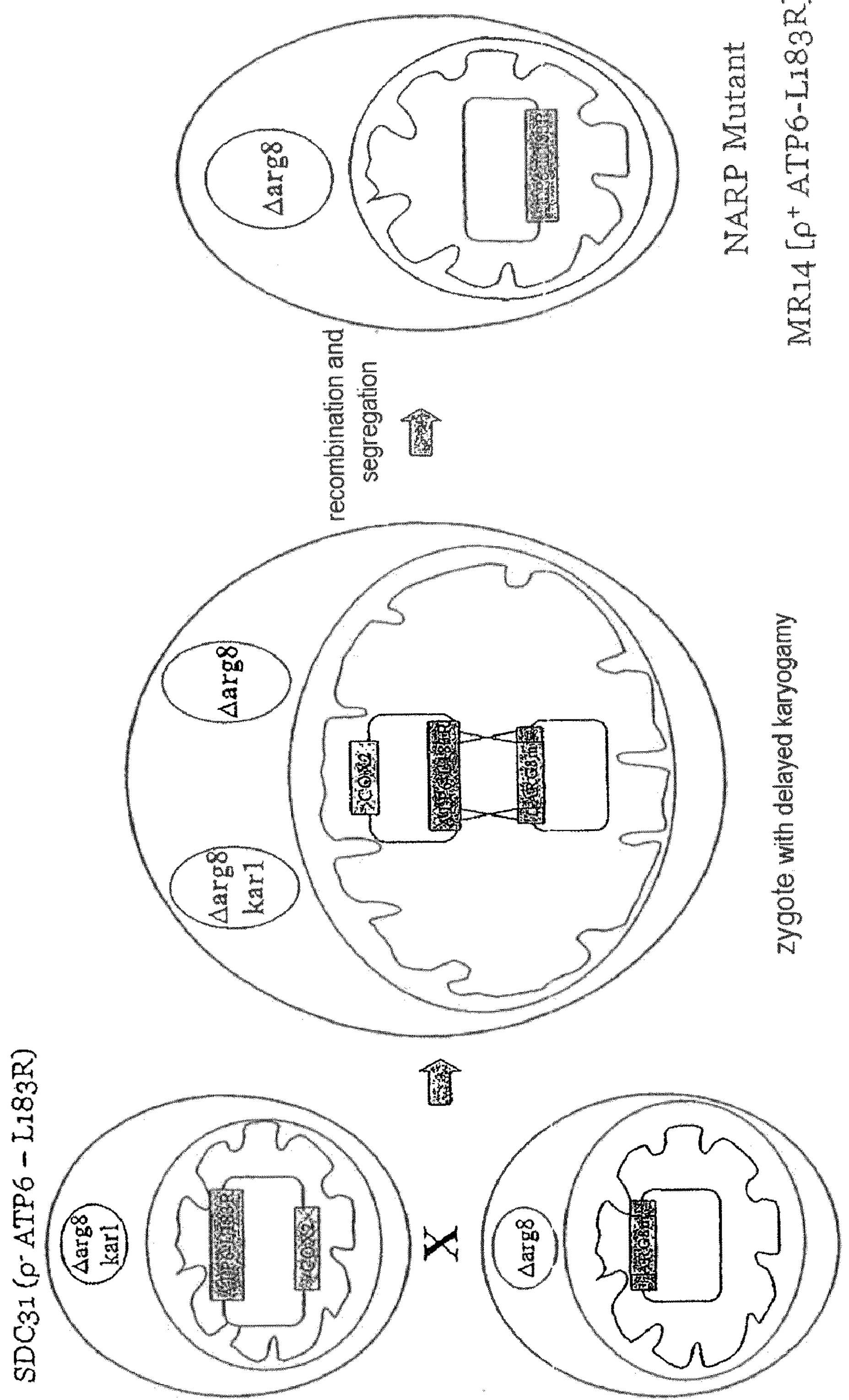
Figure 6:
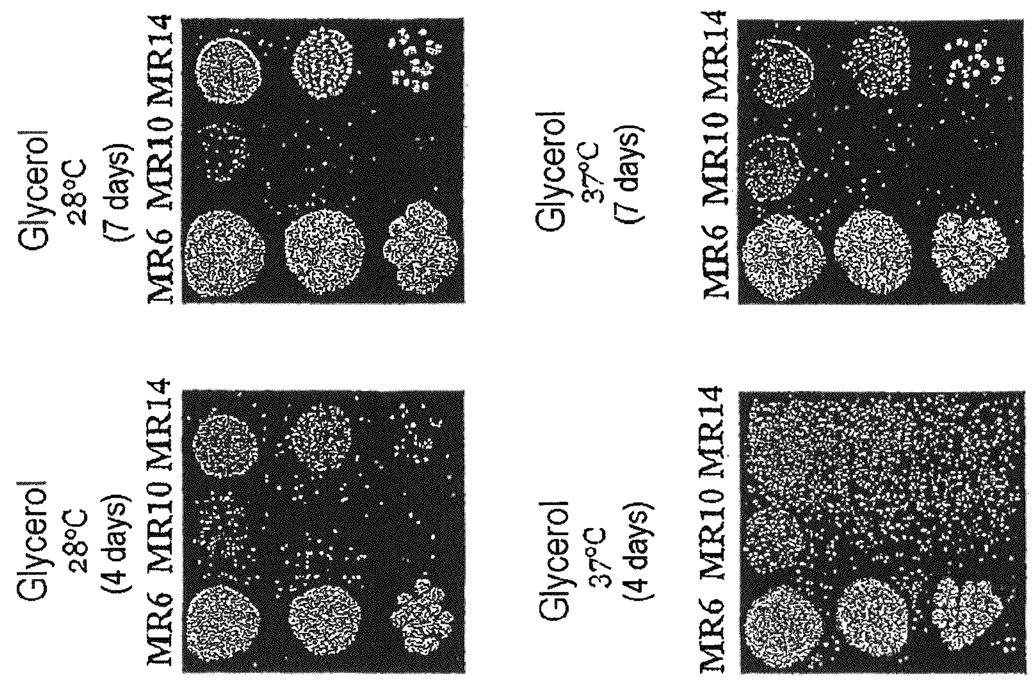
Figure 8:
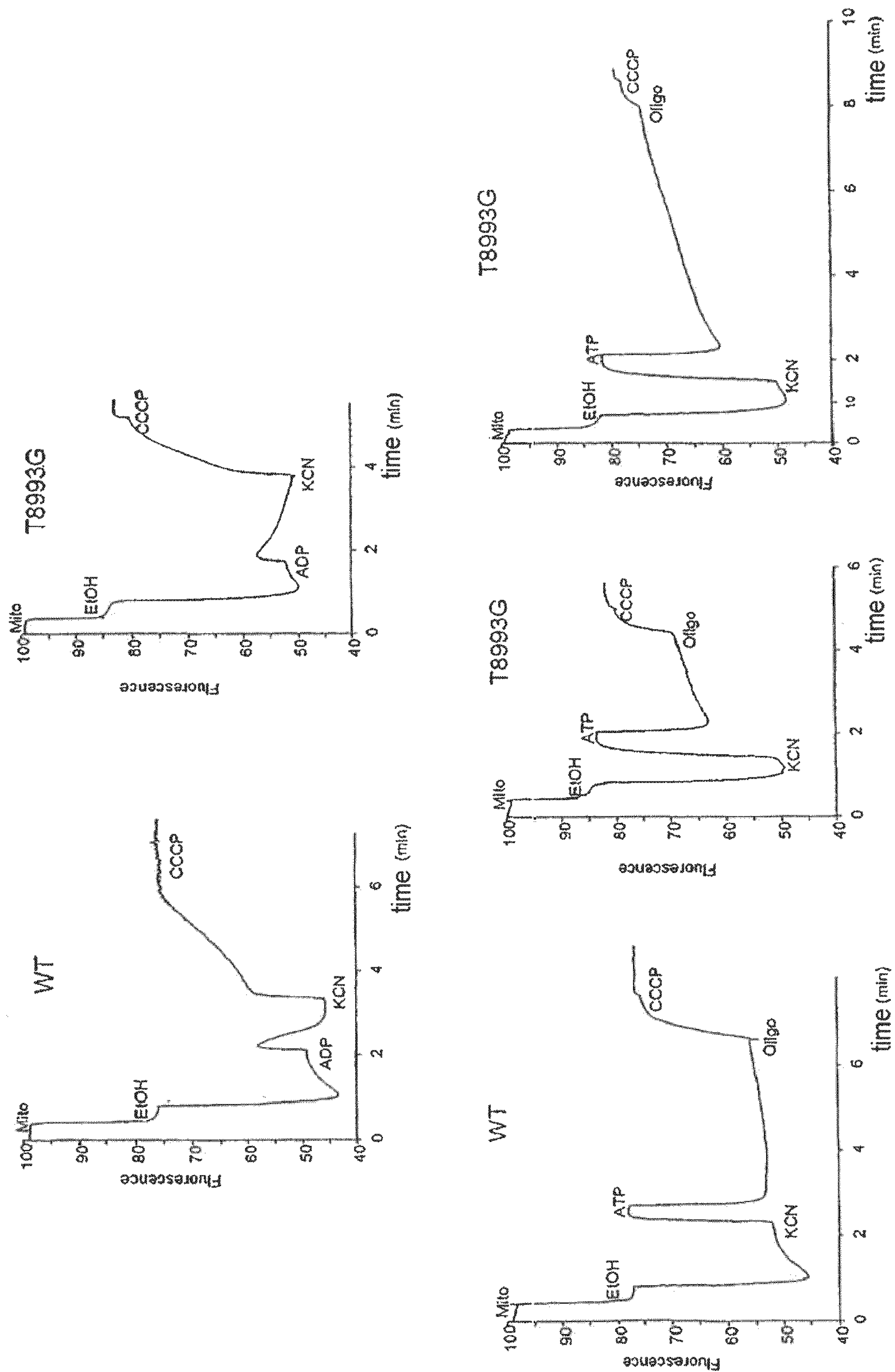
Figure 9:
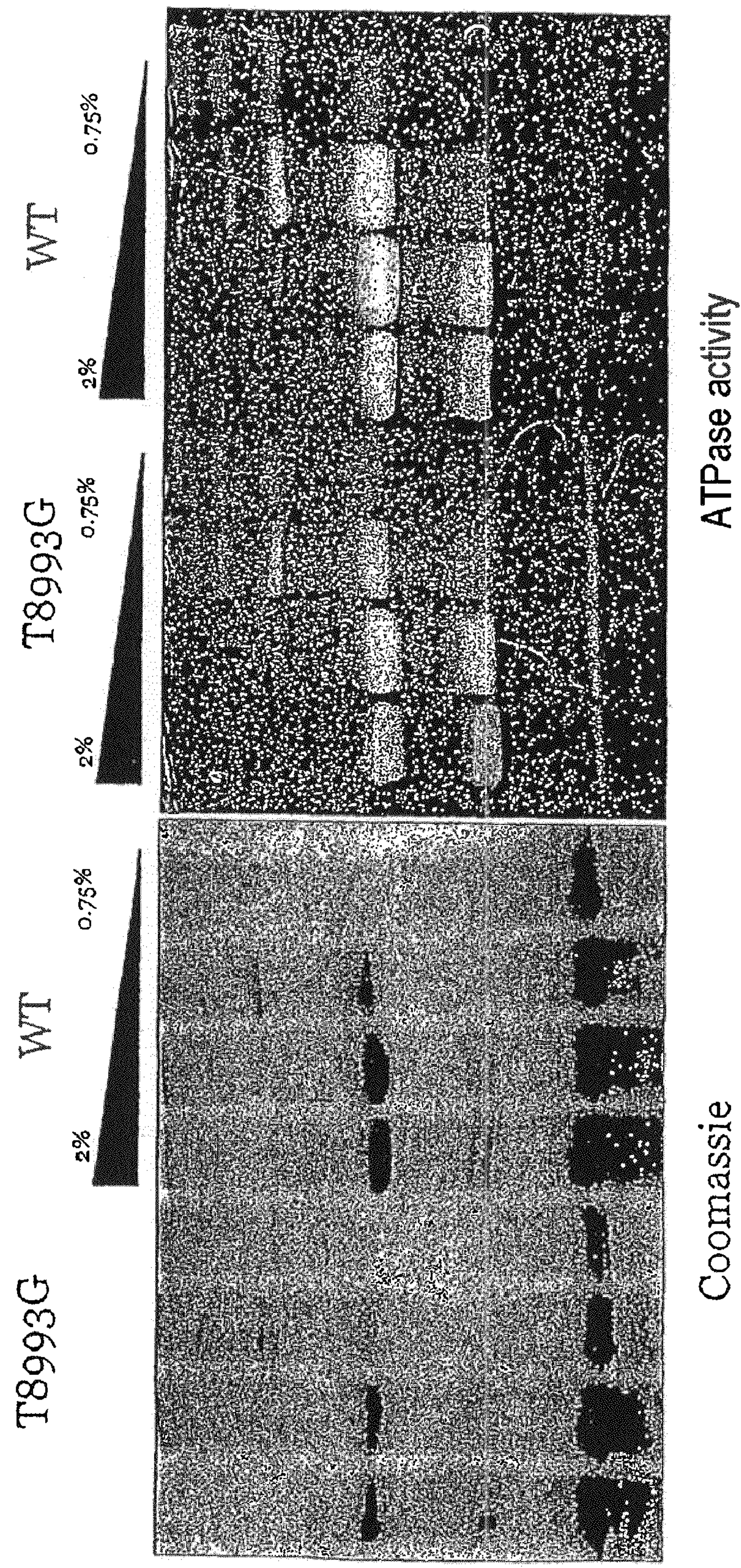
Figure 11:
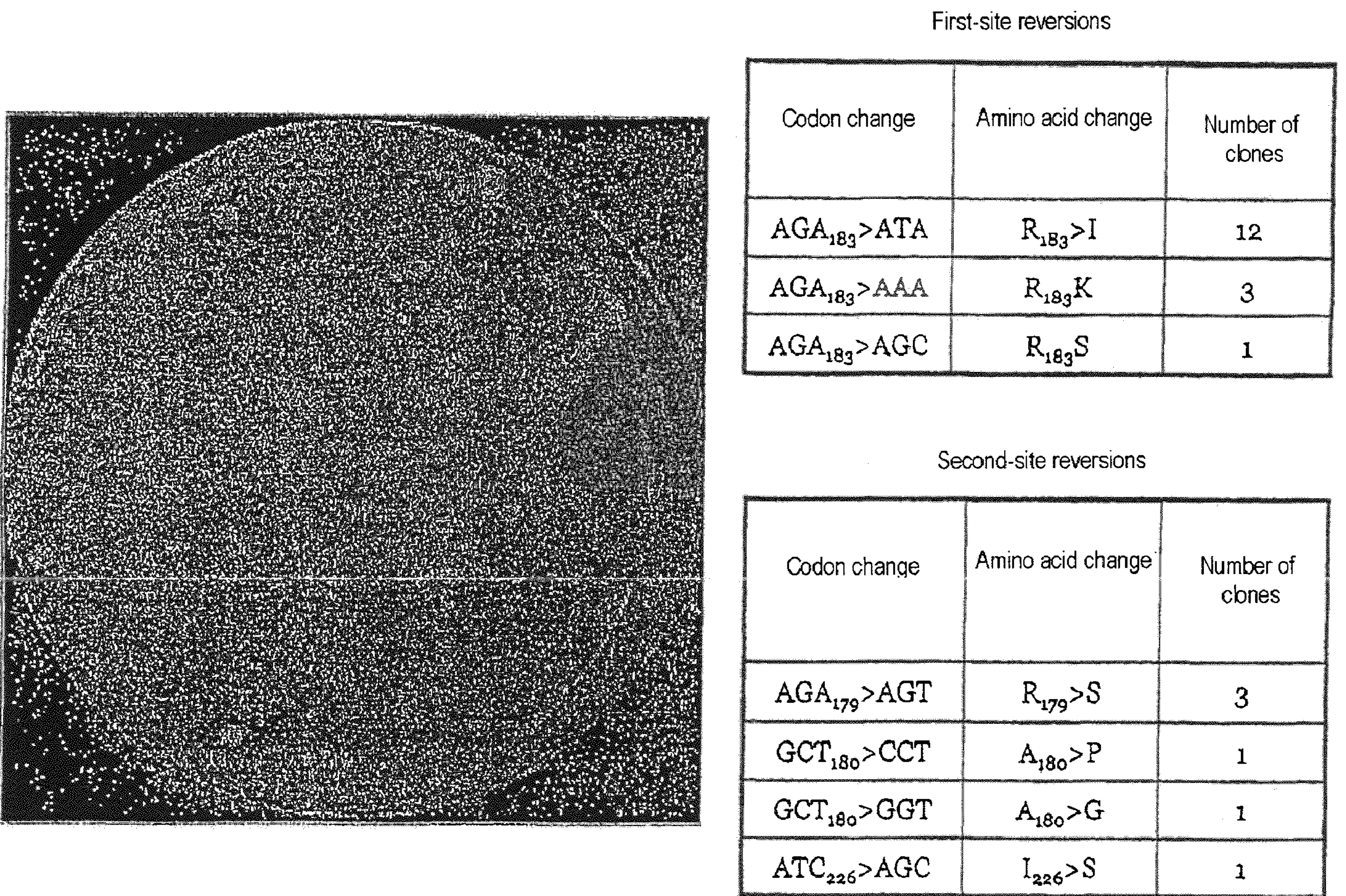
Figure 12:
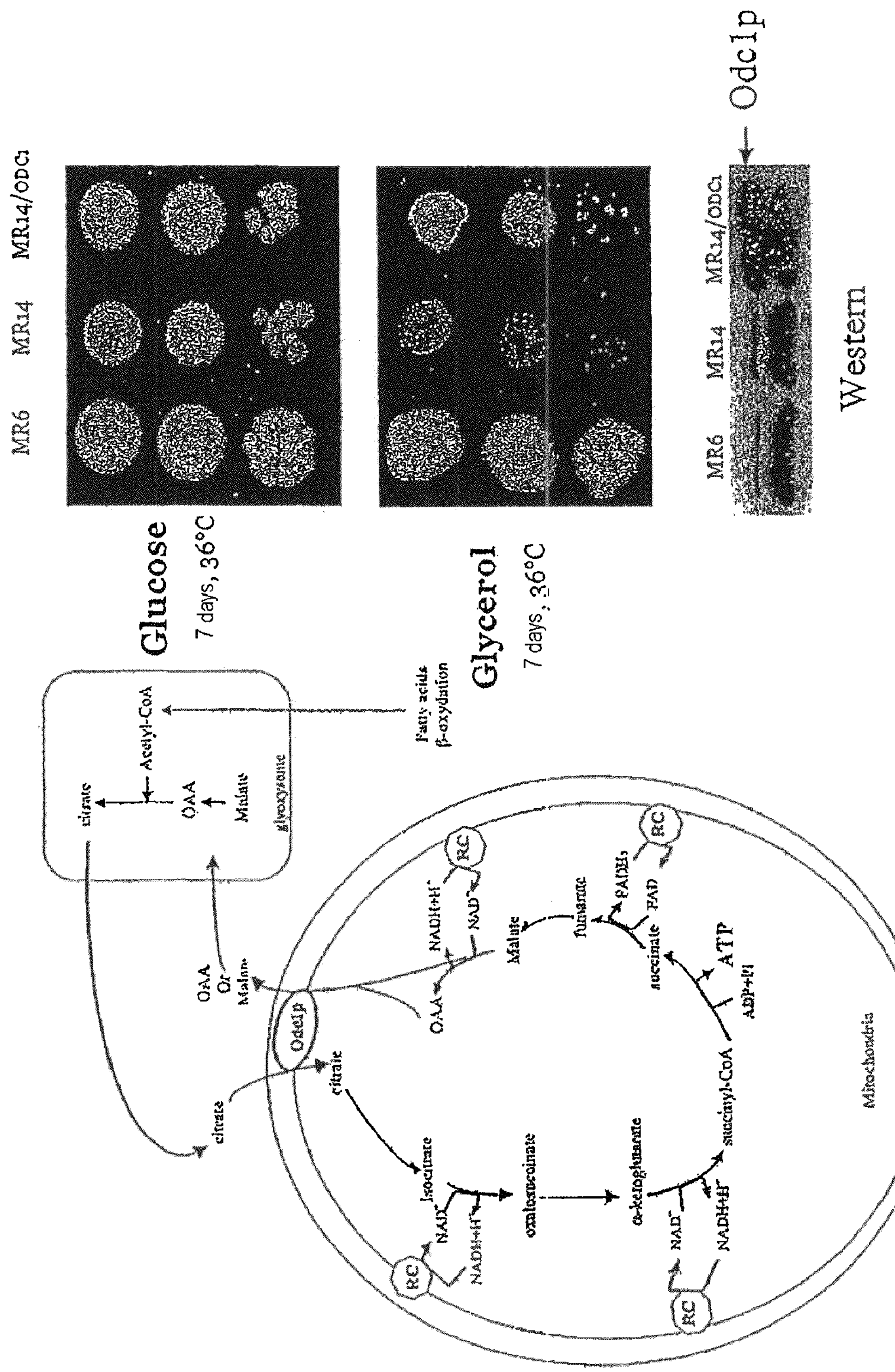

A. Construction of the MR10 mutant. The mitochondrial ATP6 gene was deleted from the MR6 strain (arg8::HIS3 [rho$^+$ FY1679]; wild-type mitochondrial genome and nuclear ARG8 gene deleted), and replaced with the ARG8$^m$ genetic marker, a mitochondrial version of the nuclear ARG8 gene which encodes a mitochondrial protein (Arg8p) involved in arginine biosynthesis. The mutant strain thus obtained is called MR10 (rho$^+$, Δatp6::ARG8m).
B. Growth phenotype of the MR10 mutant, compared to the MR6 strain. Unlike MR6, MR10 is no longer capable of growing from a nonfermentable carbon source (glycerol). On the other hand, unlike MR6, MR10 is capable of growing in the presence of glucose (fermentable sugar), without an outside supply of arginine.
C. Southern blotting analysis of the genomic DNA of the MR10 strain (rho$^+$, Δatp6::ARG8m), by comparison with the MR6 strain (rho$^+$) and a strain devoid of mitochondrial DNA (rho$^o$). The DNA digested with Swa I was hybridized with radiolabeled probes specific for the ATP6 or ARG8m gene. The hybridization signals obtained confirm the replacement of ATP6 with ARG8m in the MR10 strain.
D. Genetic complementation of the MR10 mutant. A genetic complementation test for the MR10 mutant, by crossing with a synthetic $\rho^-$ strain (SDC30) containing only the ATP6 gene in its mitochondria confirms that the respiratory growth deficiency of MR10 is indeed due to inactivation of the ATP6 gene.
E. Analysis of the proteins extracted from the MR6 and MR10 strains, by Western blotting with antibodies directed against the Atp9p and Atp6p proteins. An absence of accumulation of the Atp6p protein is observed in the MR10 strain.
F. Analysis of mitochondrial protein synthesis in the MR6 (W.T.) and MR10 (Δatp6) strains by radiolabeling and SDS-PAGE electrophoresis. An absence of Atp6p protein synthesis is observed in the MR10 strain;

FIG. 4 illustrates the strategy used to introduce mutations into the yeast ATP6 gene. The equivalent of the t8993g mutation ($tta_{183}$→$aga_{183}$; L183>R) was introduced into the yeast mitochondrial genome by crossing the SDC31 strain ($\rho^-$, ATP6-L183R) with the MR10 strain ($\rho^+$, atp6::ARG8m). In the zygotic cells derived from the crossing between SDC31 and MR10, the parental mitochondria fuse and the mitochondrial DNAs of SDC31 and MR10 can then recombine. A double crossing over results in the replacement of ARG8$^m$ with the ATP6 gene carrying the tta→aga mutation. By virtue of the karI-I mutation in the nucleus of the SDC31 strain, it was possible to obtain haploid clones which had the nucleus of the MR10 strain and the recombinant mitochondrial genome containing the mutated ATP6 gene. Having lost the ARGB$^m$ gene, the latter are incapable of growing in the absence of arginine. One of these NARP mutants ($\rho^+$, ATP6-L183R), called MR14, was selected for the subsequent analyses;

FIG. 5 illustrates the molecular and genetic analysis of the yeast t8993g mutant (MR14 mutant). A. Chromatography of the nucleotide sequence of the region of the ATP6 gene around codon 183. In the wild-type (MR6) this codon (tta) specifies a leucine residue; in the mutant (MR14), this codon is modified to aga, which specifies arginine. B. Complementation of the t8993g mutant (MR14) by crossing with a synthetic $\rho^-$ strain (SDC30) containing only the ATP6 gene in its mitochondria. The growth of MR14 on glycerol is greatly slowed. The SDC30 strain is incapable of growing on this medium. The growth on glycerol is restored by the crossing, which demonstrates that the respiratory deficiency phenotype of the MR14 mutant is indeed due to the t8993g mutation and to it alone;

FIG. 6 shows that the t8993g mutation (L183>R) severely impairs the respiratory growth of the yeast. The wild-type strain (MR6), the deletant Δatp6::ARG8$^m$ (MR10) and the MR14 mutant carrying a $tta_{183}$>aga equivalent of the t8993g mutation, were cultured at 28° C. or 37° C. in medium containing a fermentable (glucose) or nonfermentable (glycerol) carbon source. The MR14 mutant strain shows a high growth deficiency on media containing a nonfermentable carbon source (glycerol), both at 28° C. and at 37° C.; only a very slight growth on glycerol is noted after seven days of incubation, whereas the growth of the wild-type strain is already complete after barely three days. On the other hand, MR14 grows normally via the fermentative pathway (glucose);

FIG. 7 illustrates the activity of the respiratory chain and of the ATP synthase complex of the wild-type (MR6) and t8993g mutant (MR14) strains. The mitochondria were isolated from the wild-type (MR6) and t8993g mutant (MR14) strains cultured in YPGALA. The various factors were added at the following concentrations: proteins (0.15 mg/ml), NADH (state 4; 4 mM), ADP (state 3; 400 μm), oligomycin (oligo; 6 μg/ml), CCCP (3 μM), ascorbate (Asc; 15 mM), TMPD (1.4 mM). The respiratory coefficient (RCR) is the ratio of the state 3 respiration rate to the state 4 respiration rate. N: not applicable. The percentages of small $\rho^-/\rho^o$ in the cultures are indicated. In the case of the MR14 mutant, the state 4 respiration rate is close to three times lower compared with the state 4 respiration rate measured for MR6 (81 against 298 $O.min^{-1}.mg^{-1}$);

FIG. 8 illustrates the analysis of the energization of the inner mitochondrial membrane by fluorometry with rhodamine 123. Various factors were added to the intact mitochondria of the wild-type strain MR6 (WT) and of the MR14 mutant (T8993G): rhodamine 123 (0.5 μg/ml), mitochondrial proteins (Mito; 0.3 mg/ml), ethanol (EtOH; 10 μl), oligomycin (oligo; 6 μg/ml), potassium cyanide (KCN; 0.2 mM), and carbonyl cyanide m-chlorophenylhydrazone (CCCP; 3 mM);

FIG. 9 illustrates the analysis of the ATP synthase complex by the BN-PAGE technique. Mitochondria of the wild-type strain (MR6) and of the t8993g mutant were isolated and then solubilized with digitonin at the concentrations indicated. After centrifugation, the complexes were separated by BN- PAGE and the gels were stained with Coomassie blue or incubated with ATP-$Mg^{2+}$ and $Pb^{2+}$ in order to reveal the ATPase activity;

FIG. 10 illustrates the screening for molecules that act against NARP syndrome, using the yeast mutants. Step 1: the mutant is cultured in medium containing glucose. Step 2: the mutant cells are plated out in a layer at the surface of an agar medium containing glycerol as carbon source. Step 3: filters which each contain a defined amount of one of the test molecules are placed on the Petri dish, the molecules diffuse in the medium and set up a concentration gradient around the filters. Step 4: the dishes are incubated; a halo emerges around the filters containing a substance capable of counteracting the effects of the mutation (drug C5);

FIG. 11 illustrates the sequence of the t8993g-mutant revertants. Cells of the t8993g yeast mutant were plated out in a dense layer at the surface of a nutritive medium containing a nonfermentable carbon source (glycerol, medium N3), i.e. conditions which do not allow growth of the t8993g mutant. After incubation for a few days, revertant clones that have recovered a sufficient respiratory capacity are seen to appear. The ATP6 genes of these revertants were amplified by PCR and sequenced. The "first-site" suppressors result in replacement of arginine 183 with an amino acid other than the leucine present in the wild-type sequence of Atp6p, namely lysine, isoleucine or serine. The "second-site" suppressors result in replacement of arginine residue 179 with serine, of alanine residue 180 with proline or glycine, or of isoleucine residue 226 with serine;

FIG. 12 illustrates the metabolic suppression of the t8993g mutant by overexpression of Odc1p.

A. Schematic representation of the mechanism of metabolic suppression. In the whole cells, a citrate/malate or oxaloacetate counter exchange across the inner mitochondrial membrane is catalyzed by Odc1p. The citrate produced during the glyoxylate cycle is transported in the mitochondria by Odc1p (Palmieri et al., J. Biol., Chem., 2001, 276, 1916-1922) and can enter the TCA cycle (Krebs cycle) and bring about the production of succinate, coupled to substrate-level ADP phosphorylation. The malate or the oxaloacetate can subsequently then be transported to the cytosol via Odc1p and enter the glyoxylate cycle. This reaction cycle can perpetuate itself due to the production of acetyl-CoA via fatty acid degradation, which is increased due to the proliferation of peroxysomes in the cells where the retrograde response is activated (for review, see Butow, R. A. and Avadhani, N. G. *Moll. Cell* 2004, 14, 1-15). RC denotes the respiratory chain.

B. Partial complementation of the t8993g mutation by overexpression of Odcp1. The wild-type strain (MR6), the t8993g mutant strain (MR14) and the t8993g mutant strain overexpressing Odc1p (MR14/ODC1) were cultured overnight in a medium containing glucose (YPGA). The cultures were serially diluted, and a drop of each dilution was deposited on YPGA medium and medium containing glycerol as carbon source (medium N3). The dishes were subsequently incubated at 36° C. and photographed after incubation for 7 days. The analysis of the proteins extracted from the MR6, MR14 and MR14/ODC1 strains, by Western blotting with antibodies directed against Odc1p, confirms that Odcp1 is overexpressed in the MR14/ODC1 strain.

EXAMPLE 1

Introduction into the Mitochondrial Genome of *S. cerevisiae* of the ATP6 Gene Mutations Responsible for NARP Syndrome in Humans The nucleic acids are manipulated according to conventional methods, using the standard protocols as described in: *Current Protocols in Molecular Biology* (Frederick M. AUSUBEL, 2000, Wiley and son Inc, Library of Congress, USA) and *Molecular Cloning: A Laboratory Manual, Third Edition*, (Sambrook et al., 2001, Cold Spring Harbor, N.Y.: Cold Spring Harbor Laboratory Press).

1) Materials and Methods 1.1) Molecular Biology and Genetics Techniques a) Yeast and Bacterial Strains, Plasmids The following yeast and bacterial strains and plasmids were used:

MR6: mat α, ade2, leu2, ura3, trp1, his3, arg8::HIS3 [$rho^+$ FYI679]

DFS160: mat α, ade2, leu2, ura3, kar1-1, Δarg8::URA3 [$rho^o$]

SDC30: mat α, ade2, leu2, ura3, Δarg8::URA3 [$rho^-$ ATP6, COX2]

NB40-3c: mat α, lys2, leu2, ura3, his3deltaHinDIII, arg8::hisG [$rho^+$ cox2-62]

*E. coli* XL1-Blue: recA1, endA1, gyrA9, thi-1, hsdR17, supE44, relA1, lac [F' proAB lac $I^qZ\Delta M15$ Tn 10 ($Tet^r$)]

pJM2 (Mulero J J. & Fox T. D., Mol. Biol. Cell., 4, 1327-1335).

b) Culture Media for Yeast

The yeast strains are cultured in the following media:

YPGA: 1% (w/v) yeast extract, 1% bactopeptone, 2% glucose, 20 mg/l adenine

YPGALA: 1% yeast extract, 1% bactopeptone, 2% galactose, 30 mg/l adenine

N3: 1% yeast extract, 1% bactopeptone, 10 mM $Na_2HPO_4$, 40 mM $KH_2PO_4$, 20 ml/l glycerol; 2% of agar are incorporated to solidify the media.

The bacteria are cultured in LB medium: 5 g/l NaCl, 0.5% yeast extract, 0.3 N NaOH, 1% bactotryptone.

c) DNA Amplification by Polymerase Chain Reaction (PCR)

The DNA amplifications by PCR were carried out with the pFU polymerase (STRATAGENE), in 50 μl of a buffer provided by the manufacturer, containing 100 ng of the DNA carrying the nucleotide sequence to be amplified, 25 picomol of each of the two amplification primers, 200 μM of each dNTP, and one unit of enzyme. The following program was used: [95° C.-2 min; 55° C.-30 sec; 72° C.-1 min 30 sec]×1; [95° C.-30 sec; 55° C.-45 sec; 72° C.-1 min 30 sec]×28; [95° C.-30 sec; 55° C.-30 sec; 72° C.-15 min]×1.

d) Purification of DNA Fragments

The DNA fragments were separated in a 1% agarose TBE gel (89 mM boric acid, 25 mM EDTA, 89 mM Tris base) containing 0.5 μg/ml of ethidium bromide in order to visualize them under UV (254 nm). The fragments of interest were purified using the QIAquick Gel Extraction Kit® (QIAGEN), according to the supplier's instructions.

e) Dephosphorylation of the DNA Fragment Ends

The DNA fragment ends were dephosphorylated in a 20 mM Tris-HCl buffer, pH 8, containing two units of alkaline phosphatase (Calf Intestinal Phosphatase, BIOLABS), at 37° C. for one hour. The reaction was stopped by adding 2 μl of 0.5 M EDTA pH 8, and 15 μl of 10% SDS. The mixture was incubated for 15 min at 70° C. and then treated with phenol and then with chloroform. The DNA in the aqueous phase was precipitated by adding two volumes of ethanol and 1/10 of volume of 3 M sodium acetate, pH 5.2. The precipitate was washed with 70% ethanol and then vacuum-dried and taken up in water.

f) DNA Fragment Ligation

The T4 phage ligase was used to catalyze the formation of phosphodiester bonds between DNA fragments, according to the recommendations of the supplier (GIBCO).

g) Mutagenesis

The site-directed mutagenesis is carried out on the gene cloned into a plasmid, using the Gene Editor In Vitro Site-Directed Mutagenesis System® kit (PROMEGA) according to the supplier's instructions.

h) Transformation of Bacteria by Electroporation

The *E. coli* strain XL1-Blue is cultured in LB medium, at 37° C., with shaking, until an $OD_{600nm}$ of 0.5 to 1 is reached. The cells are washed several times with sterile water at 4° C., and then concentrated in a solution of glycerol at 10% (w/v). The cells thus prepared are aliquoted and stored at −80° C. The electroporation is carried out using the ECM 395 machine (BTX). 40 μl of competent cells are mixed with 100 ng of plasmid DNA and subjected to an electrical discharge (2.5 kV), and then LB medium is added. The cell suspension is subsequently incubated for 1 hour at 37° C. and then plated out on LB medium containing 100 μg/ml of ampicillin, for selection of the transformants.

i) Plasmid DNA Preparation

The plasmids are amplified in the *E. coli* strain XL1-Blue transformed by electroporation, as specified in h). The plasmid DNA is subsequently extracted from the bacteria, using the Plasmid Midi Kit® (QIAGEN), according to the supplier's recommendations.

j) Conventional Transformation of Yeast Cells (Nuclear Transformation)

The day before the experiment, drops of a fresh culture of cells to be transformed are deposited onto YPGA medium. The following day, cells are sampled with a toothpick and mixed with 100 μl of a 0.2 N lithium acetate, pH 5, 40% polyethylene glycol 4000, 100 mM DTT buffer containing 50 μg of carrier DNA predenatured at 100° C. for 20 min, and 50 ng to 1 μg of DNA of the plasmid being introduced into the cells. After incubation for 30 min at 45° C., the cells are washed with Ringer buffer, and then plated out onto a medium suitable for selection of the transformants.

k) Obtaining Mitochondrial Transformants

The plasmid DNA is introduced into the mitochondria of a yeast strain (DFS160) entirely devoid of mitochondrial DNA ($\rho^o$), by biolistic bombardment, using the Biolistic PDS-1000/He™ system (BIO-RAD), according to the protocol previously described (Bonnefoy, N. and Fox, T. D., Methods Cell Biology, 2001, 65, 381-396).

l) Crossing of the Yeast Strains and Isolation of the Haploid Cytoductant Recombinants The procedure used is that described in (Bonnefoy, N. and Fox, T. D., Methods Cell Biology, 2001, 65, 381-396).

m) Analysis of Yeast Genomic DNA by Southern Blotting

The yeast genomic DNA extractions were carried out on cells cultured overnight in YPGA medium. The cells are harvested by centrifugation and then taken up in 0.2 ml of 0.1 M NaCl buffer containing 2% of Triton-X100, 1% of SDS and 0.2 ml of a phenol/chloroform/isoamyl alcohol mixture (50/48/2). 500 μl of glass beads (diameter 0.45 mm) are added. The mixture is vortexed for 2 min, and then 0.2 ml of 10 mM TrisHCl buffer, pH 8, 1 mM EDTA are added. The aqueous phase is then separated by centrifugation (5 min at 10 000×g) and the nucleic acids that it contains are precipitated by adding 20 μl of 8 M ammonium acetate and 1 ml of ethanol. The precipitate is harvested by centrifugation, washed with 70% ethanol, then taken up and incubated for 15 min at 37° C. in 400 μl of 10 mM TrisHCl, pH 8, 1 mM EDTA, containing 30 μg of Rnase A. The DNA of the sample is precipitated by adding 2.5 volumes of ethanol and 1/10 volume of 3 M sodium acetate at pH 5.2. It is washed with 70% ethanol, dried, and finally taken up in 50 μl of water.

The DNA is digested with the appropriate restriction enzymes and the resulting DNA fragments are separated by agarose gel electrophoresis, blotted onto a nitrocellulose membrane and hybridized with a specific radiolabeled probe. The membrane is then autoradiographed in order to visualize the fragments of interest.

n) Genetic Complementation Test

The respiration-deficient yeast mutant and the synthetic $\rho^-$ strain containing only the ATP6 gene in its mitochondria (SDC30 strain) are cultured separately, overnight, in an agar medium (YPGA). A "drop-to-drop" crossing is subsequently carried out on YPGA medium. After incubation overnight, the crossing is replicated using pieces of velvet on a medium containing glycerol (N3). The presence of cells derived from the crossing, capable of growing on glycerol, indicates the presence of recombinants which have reconstituted a wild-type mitochondrial genome by recombination of the mitochondrial DNA of the two strains.

1.2) Biochemistry Techniques a) Extraction of Total Yeast Proteins

The cells are cultured in YPGALA medium and harvested when the absorbance is 2 units of optical density (OD) at 650 nm. The cells are washed twice with water and then taken up with water at a density of 10 OD/ml. Cell lysis is obtained by adding 150 μl of 1.85 M NaOH buffer containing 7.4% β-mercaptoethanol to 1 ml of cell suspension. Incubation for 10 min at 4° C. is carried out and then 150 μl of 3M trichloroacetic acid (TCA) are added in order to precipitate the proteins. A further incubation for 10 min at 4° C. is carried out and then the mixture is centrifuged for 5 min at 10 000×g. The pellet is washed with acetone at −20° C. in order to remove all traces of TCA. The pellet is subsequently taken up in 250 μl of 5% SDS, treated with ultrasound, and then incubated for 5 min at 100° C. The protein sample is finally harvested by centrifugation (5 min at 10 000×g).

b) Analysis of Mitochondrial Protein Synthesis by Incorporation of Methionine and Cysteine Radiolabeled with $^{35}S$ The procedure is that described by Lefebvre-Legendre et al., J. Biol. Chem., 2001, 276, 6789-6796. The experiment is carried out with cells in the exponential growth phase, in YPGALA medium. The cells are washed with water and then taken up and incubated for 40 min in 1×LSM containing 1% galactose and the nutrients corresponding to the auxotrophic markers of the strain to be analyzed (10×LSM: 5 mg/l $H_3BO_3$, 0.33 mg/l $CuCl_2$, 1 mg/l KI, 5.2 mg/l $MnCl_2.4H_2O$, 2.35 mg/l $Na_2MoO_4.2H_2O$, 3.4 mg/l $ZnCl_2$, 2 mg/l $FeCl_3.6H_2O$, 20 mg/l calcium pantothenate, 20 mg/l thiamine chloride, 20 mg/l pyridoxine, 5 mg/l nicotinic acid, 0.2 mg/l biotin, 200 mg/l mesoinositol, 54 g/l $(NH_4)H_2PO_4$, 3.65 g/l $MgCl_2.6H_2O$, 14.58 g/l $NH_4Cl$, 9 g/l $KH_2PO_4$, 0.9 g/l NaCl, 1.188 g/l $CaCl_2.2H_2O$). This step is intended to cause a cysteine and methionine deficiency in the cells. Cycloheximide is subsequently added at a final concentration of 250 μg/ml, in order to inhibit the extramitochondrial cytosolic protein synthesis; the radioactivity is therefore incorporated only into the proteins encoded by the mitochondrial genome. After 5 min, 0.5 mCi of promix (L-[$^{35}S$] methionine and L-[$^{35}S$] cysteine, AMERSHAM) is added and the sample is incubated for 10 min at 30° C. A 1% solution of casamino acids is added in order to stop the incorporation of the radiolabeled amino acids and to allow termination of the translation products. The cells are harvested and washed twice successively in the 1% casamino acid solution, and then taken up in 0.25 M mannitol, 20 mM Tris-sulfate, pH 7.4, 1 mM EDTA, 1 mM PMSF buffer. Glass beads (0.45 mm in diameter) are added and the samples are vortexed for 5 min in order to grind the cells. The ground material is centrifuged at low speed (5 min at 750×g at 4° C.) in order to remove the cell debris. The supernatant is centrifuged at high speed (12 000×g at 4° C. for 20 min) in order to harvest the mitochondrial membranes. The radioactivity of the samples is measured and the radiolabeled proteins that they contain are subsequently analyzed in an SDS-PAGE gel followed by autoradiography of the gel.

c) Electrophoresis, Immunodetection and Assaying of Proteins

The denaturing acrylamide gel protein electrophoresis (SDS-PAGE) was carried out according to the procedure of Laemmli, Nature, 1970, 227, 680-685. The nondenaturing gel electrophoresis technique (BN-PAGE) used is that described by Schagger et al., Anal, Biochem, 1994, 217, 220-230. The ATPase activity of the BN-PAGE gels was detected by the method described by Grandier-Vazeille and Guerin, Anal. Biochem., 1996, 242, 248-254. The detection of proteins on a nitrocellulose membrane with specific antibodies was carried out with the technique described by Paumard et al., EMBO J., 2002, 21, 221-230. The antigene-antibody complexes were revealed with the ECL+® kit (AMERSHAM). The proteins were assayed with the method of Lowry et al., J. Biol. Chem., 1951, 193, 265-275.

2) Results a) Construction of the MR10 Mutant Yeast by Deletion of the Mitochondrial ATP6 Gene and Replacement with the ARG8$^{m}$ Genetic Marker The ATP6 gene is, in yeast, as in humans, located in the mitochondrial genome. In yeast, ATP6 is part of a polycistronic transcription unit containing the COX1 gene (encoding a subunit of complex IV), the ATP8 gene (encoding a subunit of ATP synthase) and, in certain strains, the ENS2 gene which encodes an endodeoxyribonuclease (FIG. 3A). In humans, the main mutation responsible for NARP syndrome is a simple nucleotide change (t to g) at position 8993 of the mitochondrial genome (denoted t8993g). This change results in the leucine residue 156 of the human Atp6p protein being replaced with arginine (FIG. 2). This leucine residue is conserved in the yeast Atp6p protein, but in a different position (at 183). In order to obtain the replacement of this residue with arginine in the yeast, a double nucleotide change is necessary: tta→aga. In addition, other mutations associated with NARP syndrome have been detected in humans: t8993c, t9176g, t9176c and t8851c (table I).

In order to facilitate the introduction of the mutations into ATP6, a yeast strain (MR10) was first of all constructed from the MR6 strain (wild-type mitochondrial genome and nuclear ARG8 gene deleted; arg8::HIS3 [rho$^{+}$FY1679]). In MR10, the ATP6 gene has been deleted and replaced with the ARG8m gene, a genetic marker independent of respiratory function (Bonnefoy, N. and Fox. T. D., Methods Cell Biology, 2001, 65, 381-396). The ARG8m gene is a mitochondrial version (recoded version) of the nuclear ARG8 gene, which encodes a mitochondrial protein (Arg8p) involved in arginine biosynthesis.

A cassette for inactivation of the ATP6 gene with ARG8$^{m}$ (atp6::ARG8m) was constructed by PCR, with the oligonucleotides:

```
ATP6-PRO (SEQ ID NO: 3):
gcgggatcctttattatagtttaatactccatatgtaaattattttatt

tataattttattttataatttaagcatatacagcttcg,
and

ATP6-Ter (SEQ ID NO: 4):
gcctagataataagatataattatgattaattattataagttatatagtt

ttataaatttataattattatgacacatttagaaagaa.
```

These oligonucleotides carry, at their 5' end, respectively a BamH I and Xba I site. The PCR product was digested with BamH I and Xba I and then cloned at the BamH I and Xba I sites of the plasmid pJM2, previously described (Mulero, J. J. & Fox, T. D., Mol. Cell. Biol., 1993, 4, 1327-1335). The resulting plasmid was introduced by bombardment into the rho° mitochondria of the DFS160 strain. The resulting synthetic $\rho^{-}$ strain was crossed with the MR6 strain. In the zygotic cells, the parental mitochondria fuse and the parental mitochondrial DNAs can then recombine. A double crossing-over results in the replacement of ATP6 with ARG8$^{m}$. The DFS160 strain carries the nuclear mutation kar1-1, the effect of which is to delay nuclear fusion, and results in the production of haploid clones (Bonnefoy, N. and Fox, T. D., 2001, Methods Cell Biology, 2001, 65, 381-396). Haploid clones having the nucleus of the MR6 strain and the recombinant mitochondrial genome Δatp6::ARG8m were thus obtained. One of these clones, called MR10 (mat α, ade2, leu2, ura3, trp1, his3, arg8::HIS3 [rho+ FY1679; Δatp6::ARG8m]), was selected for the subsequent analyses.

b) Genetic and Molecular Analysis of the MR10 Mutant

The analysis of the growth phenotype of the MR10 mutant, compared with the MR6 strain (FIG. 3B), shows that MR10 is no longer capable of growing from a nonfermentable carbon source (glycerol). On the other hand, unlike MR6, MR10 is capable of growing in the presence of glucose (fermentable sugar), without an external supply of arginine.

Analysis of the genomic DNA of the MR6 and MR10 strains and of a strain devoid of mitochondrial DNA (rho°) digested with Swa I, by Southern blotting with radiolabeled probes specific for the ATP6 or ARG8m gene, confirms the replacement of ATP6 with ARG8m in the MR10 strain (FIG. 3C).

Genetic complementation of the MR10 mutant, by crossing with a synthetic $\rho^{-}$ strain (SDC30) containing only the ATP6 gene in its mitochondria, confirms that the respiratory growth deficiency of MR10 is indeed due to inactivation of the ATP6 gene (FIG. 3D).

The analysis of the proteins extracted from the MR6 and MR10 strains, by Western blotting with antibodies directed against the Atp9p and Atp6p proteins, demonstrates the absence of Atp6p protein accumulation in the MR10 strain (FIG. 3E).

The analysis of the mitochondrial protein synthesis in the MR6 and MR10 strains by radiolabelling and SDS-PAGE electrophoresis demonstrates the absence of Atp6p protein synthesis in the MR10 strain (FIG. 3F).

c) Construction of Yeast ATP6 Gene Mutants Carrying Mutations Responsible for NARP Syndrome in Humans The equivalent of each of the five mutations responsible for NARP syndrome in humans (table I) was introduced separately into the yeast ATP6 gene cloned into the plasmid pJM2. The yeast ATP6 gene was amplified with the oligonucleotides ATP6-up (SEQ ID NO: 5: gcggaccccaaaggaggag) and ATP6-down (SEQ ID NO: 6: cgggatcccagtggggaaggagtgaggt) which each carry a BamH I restriction site at their 5' end. The PCR product was digested with BamH I and then cloned at the BamH I site of pJM2, so as to give the plasmid pSDC21. The mutations were subsequently introduced separately into the ATP6 gene cloned into the plasmid pSDC21. The five plasmids carrying the various mutations (t8993g (pSDC22), t8993c, t9176g, t9176c and t8851c) were subsequently introduced separately by biolistic bombardment, into the mitochondria of a yeast strain (DFS160) entirely devoid of mitochondrial DNA ($\rho^{o}$). The resulting five synthetic rho$^{-}$ strains each containing one of the various mutated plasmids in their mitochondria were isolated; the strain containing the plasmid pSDC22 in its mitochondria was called SDC31 (mat α, ade2, leu2, ura3, Δarg8:: URA3 [rho$^-$ atp6 t8993g, COX2] or (ρ$^-$, ATP6-L183R)).

d) Construction of the Yeast Mutants by Introduction of the Mutated ATP6 Gene into the Mitochondrial Genome of the MR10 Mutant The five mutations were subsequently introduced into the yeast mitochondrial genome by crossing of the five mitochondrial transformants (ρ$^-$; ATP6-L183R (SDC31); ρ$^-$, ATP6-L183P; ρ$^-$, ATP6-L247R; ρ$^-$, ATP6-L247P; ρ$^-$, ATP6-L136R) with the MR10 strain (ρ$^+$, Δatp6::ARG8m). In the zygotic cells derived from the crossing between the synthetic rho$^-$ (SDC31 in the case of the L183R mutation) and MR10 strains, the parental mitochondria fuse (FIG. 4). This results in contact between the mitochondrial DNAs of the synthetic rho$^-$ (SDC31) and MR10 strains, and said DNAs can then recombine. A double crossing-over results in the replacement of ARG8$^m$ with the ATP6 gene carrying one of the five mutations. By virtue of the kar1-1 mutation in the nucleus of the synthetic rho$^-$ strains (SDC31), it was possible to obtain haploid clones having the nucleus of the MR10 strain and the recombinant mitochondrial genome containing the mutated ATP6 gene. Having lost the ARG8$^m$ gene, the latter are incapable of growing in the absence of arginine. For each of the mutations, one of the recombinants (MR14, RKY20-1, RKY-25-4, RKY38-1 and RKY39-1; table I) was selected for the subsequent analyses.

e) Genetic and Molecular Analysis of the ATP6 Gene Mutants

The region of the ATP6 gene around the mutation was sequenced in MR6 (wild-type) and in the mutants. The chromatograph (FIG. 5A) shows the presence in the wild-type of a codon (tta) which specifies a leucine residue; in the mutant (MR14), this codon is modified to aga which specifies arginine.

The growth of the t8893g (MR14), t9176g (RKY25-4) and t8851c (RKY39-1) mutants on glycerol is greatly slowed (FIG. 5B, table I). The SDC31 strain (ρ$^-$, ATP6-L183R) is incapable of growing on this medium (FIG. 5B). On the other hand, the t8993c (RKY20-1) and t9176c (RKY38-1) mutants have no marked effect on the respiratory growth of the yeast (table I).

The complementation test of the mutation by crossing with a synthetic ρ$^-$ strain (SDC30) containing only the ATP6 gene in its mitochondria shows that growth on glycerol is restored by the crossing (FIG. 5B). This test demonstrates that the respiratory deficiency phenotype of the mutant is indeed due to the mutation and to it alone.

EXAMPLE 2

Analysis of the Effects of the ATP6 Gene Mutations in Yeast

1) Materials and Methods a) Extraction of Yeast Mitochondria

The method used to extract the mitochondria is that described by Guerin et al., Methods Enzymol., 1979, 55, 149-159. The yeast, in the exponential growth phase in YPGALA medium, are harvested by centrifugation (5 min at 2000×g), washed with water, and then taken up and incubated for 10 min at 30° C. in 0.1 M Tris-HCl buffer, pH 9.3, containing 0.5 M β-mercaptoethanol. The cells are subsequently washed with 10 mM Tris-HCl buffer, pH 7, containing 0.5 M KCl, then resuspended and incubated for 20 to 40 min at 30° C. in 30 mM sodium phosphate buffer, pH 5.8, containing 1.35 M sorbitol, 1 mM EGTA and 10 mM citric acid (10 ml per gram of dry weight) and containing 2 mg/ml of 20 000 U zymolyase (ICN). At this stage, the cells are called protoplasts, i.e. cells whose wall has been digested. The protoplasts are harvested by centrifugation (5 min at 750× g at 4° C.) and then washed with 10 mM Tris-maleate buffer, pH 6.8, containing 0.75 M sorbitol, 0.4 M mannitol and 0.1% (w/v) BSA. They are subsequently lysed with a 10 mM Tris-maleate buffer, pH 6.8, containing 0.6 M mannitol and 2 mM EGTA. The mitochondria of the resulting lysate are subsequently recovered by differential centrifugation. A first low-speed centrifugation (10 min at 750×g) makes it possible to remove the nuclei and cell wall debris, whereas the mitochondria remain in the supernatant fraction. The latter is removed and then centrifuged at high speed (10 min at 12 000×g) so as to harvest the mitochondria. The mitochondrial pellet is taken up in 10 mM Tris-maleate buffer, pH 6.8, containing 0.6 M sorbitol and 2 mM EGTA.

b) Measurement of the Mitochondrial Oxygen Consumption Rate

The mitochondrial oxygen consumption rate is measured by polarography with a Clark electrode (GILSON) in 0.6 M mannitol/0.3 mM EGTA/10 mM Tris-maleate buffer, pH 6.8, containing 3 mM of Pi/Tris, pH 6.8, according to the procedure described by Rigoulet, M. and Guerin, M., FEBS Lett., 1979, 102, 18-22.

c) Analysis of the Mitochondrial Electrical Potential

The variations in mitochondrial potential were analyzed with rhodamine 123 (SIGMA) in 0.6 M mannitol/0.3 mM EGTA/10 mM Tris-maleate buffer, pH 6.8, containing 3 mM of Pi/Tris, pH 6.8, with an SFM25 fluorimeter (KONTRON), according to the procedure described by Emaus et al., Biochem. Biophys. Acta, 1986, 850, 436-448.

d) Measurement of Mitochondrial ATP Synthesis and Hydrolysis Activity

The mitochondrial ATP hydrolysis activity was measured in a 10 mM Tris-HCl buffer, pH 8.4, containing 0.2 M KCl and 3 mM $MgCl_2$, in the presence or absence of oligomycin, according to the procedure described by Somlo M., Eur. J. Biochem., 1968, 5, 276-284. The mitochondrial ATP synthesis activity was measured according to the protocol described in Schwimmer et al., J. Biol. Chem., 2005, 280, 30751-30759. More specifically, this mitochondrial ATP synthesis activity is measured in 0.6 M mannitol/0.3 mM EGTA/10 mM Tris-maleate buffer, pH 6.8, containing 3 mM of Pi/Tris, pH 6.8, with NADH (4 mM) as respiratory substrate and in the presence of ADP (1 mM). After the addition of the ADP, a fraction of the reaction medium is sampled every 15 seconds (from 1 to 2 min) and immediately mixed with perchloric acid (7%) and EDTA (25 mM). The samples are centrifuged (5 min at 15 000 g) and the supernatants are adjusted to pH 6 with a 2N solution of KOH containing 0.3 M of 3-morpholinopropanesulfonic acid. The ATP of the samples is measured by bioluminescence, using the kit provided by BIOTHEMA.

e) Nondenaturing Gel Electrophoresis (BN-PAGE Technique)

Mitochondria of the wild-type strain (MR6) and of the t8993g mutant were isolated and then solubilized with digitonin (0.75% to 2% w/v). After centrifugation, the complexes were separated by nondenaturing gel electrophoresis (BN-PAGE technique), according to the procedure described by Paumard et al., EMBO, J., 2002, 21, 221-230, and then the gels were stained with Coomassie blue.

2) Results a) Effect of the Mutations on the Respiratory Growth of the Yeast

The wild-type strain (MR6), the deletant Δatp6::ARG8m (MR10) and the t8993g (MR14), t8993c (RKY20-1), t9176g (RKY25-4), t9176c (RKY38-1) and t8551c (RKY39-1) mutants were cultured overnight in a medium containing glucose (YPGA). The cultures were serially diluted, and a drop of each dilution was deposited onto YPGA medium and a medium containing glycerol as carbon source (N3). The dishes were subsequently incubated at 28° C. or 37° C. and photographed after incubation for 4 and 7 days; the YPGA dish was photographed after incubation for 4 days at 28° C. (FIG. 6, table I).

TABLE I

Effect of the ATP6 gene mutations on respiratory growth of the yeast

| Yeast strain | Nucleotide change in humans | Amino acid change in humans | Corresponding codon change in the yeast | Corresponding amino acid change in the yeast | Respiratory growth at 28° C. |
|---|---|---|---|---|---|
| Wild-type (MR6) | | | | — | +++ |
| MR14 | t8993g | L156 > R | $tta_{183}$ > aga | L183 > R | −/+ |
| RKY20-1 | t8993c | L156 > P | $tta_{183}$ > cca | L183 > P | +++ |
| RKY25-4 | t9176g | L217 > R | $tta_{247}$ > aga | L247 > R | − |
| RKY38-1 | t9176c | L217 > P | $tta_{247}$ > cca | L247 > P | +++ |
| RKY39-1 | t8851c | W109 > R | $tta_{136}$ > aga | W136 > R | −/+ |

The MR14 mutant strain carrying an equivalent ($tta_{183}$>aga) of the t8993g mutation shows a high growth deficiency on media containing a nonfermentable carbon source (glycerol), both at 28° C. and at 37° C.; only very slight growth is noted on glycerol after incubation for seven days, whereas the growth of the wild-type strain is already complete after barely three days (FIG. 6). On the other hand, MR14 grows normally via the fermentative pathway (glucose) (FIG. 6). The respiratory growth deficiency of MR14 is completely complemented by growth with SDC30, a strain (synthetic $\rho^-$) containing only the ATP6 gene in its mitochondria (FIG. 5). This makes it possible to conclude that the t8993g mutation, and it alone, is indeed responsible for the respiratory growth deficiency observed.

Just like the t8993g mutation, the t9176g and t8851c mutations affect the respiratory growth of the yeast very severely (table I).

On the other hand, the t8993c and t9176c mutations have no marked effect on the respiratory growth of the yeast (table I).

b) Influence of the t8993g Mutation on Respiratory Activity

The mitochondria were isolated from the MR14 strain carrying the t8993g mutation and from the parental MR6 strain (the two strains differ genetically only in terms of the t8993g mutation). The mitochondrial oxygen consumption rate (respiration) was subsequently measured by oxygraphy. Briefly, NADH is added to the mitochondrial suspension, as respiratory substrate. ADP is then added in order to establish state 3 (phosphorylating state). After this addition, an increase in respiration rate is normally noted following consumption of the electrochemical proton gradient by ATP synthase, which phosphorylates the added ADP. The respiratory chain then functions more rapidly so as to compensate for this proton consumption. When all the added ADP has been phosphorylated, the respiration rate decreases and returns to the basal state (nonphosphorylating state 4). The ratio of the state 3 and state 4 respiration rates (which is referred to as respiratory control ratio, RCR) for the MR6 wild-type strain had a value of 2.4, which is typical for wild-type mitochondria (FIG. 7). In the case of the MR14 mutant, the state 4 respiration rate is close to three times lower compared with the state 4 respiration rate measured for MR6 (81 against 298 $O.min^{-1}.mg^{-1}$). Furthermore, it is noted that adding ADP has little effect on the respiration rate. In the presence of an uncoupling agent (CCCP: carbonyl cyanide m-chlorophenylhydrazone) which is a proton ionophore which allows protons to pass freely across the membrane, the respiration rate is at a maximum (Vmax). The respiration rate is stimulated by a factor of 4 (compared with state 4) in the wild-type. Stimulation of respiration in the mutant in similar proportions is also noted.

c) Measurement of ATP Synthesis by the ATP Synthase Complex

The activity of ATP synthesis by the ATP synthase complex was measured in the presence of an excess of ADP, i.e. in state 3 (phosphorylating state). The measurement is carried out in the presence and absence of oligomycin, a specific inhibitor of the ATP synthase proton channel, so as to determine the proportion of the rate of ATP synthesis measured which is due to the activity of the ATP synthase complex (other intramitochondrial reactions are capable of synthesizing ATP). For the parental strain, the value obtained was 737±45 $nmol.min^{-1}.mg^{-1}$ (FIG. 7). Under these conditions, the rate of ATP synthesis was much lower in the mutant, 59±7 $nmol.min^{-1}.mg^{-1}$ (FIG. 7).

d) Analysis of the Mitochondrial Electrical Potential

The mitochondrial electrical potential was analyzed by a technique using Rhodamine 123, a fluorescent probe sensitive to this potential (FIG. 8). An increase in the mitochondrial potential brings about entry of Rhodamine 123 into the mitochondria, accompanied by a decrease in fluorescence, due to the fact that the Rhodamine 123 is trapped in the mitochondria. Thus, variations in the mitochondrial potential can be detected by measuring variations in fluorescence. More specifically, ethanol is added to the mitochondria so as to cause the respiratory chain to operate, thereby causing energization of the inner membrane and therefore a decrease in fluorescence (FIG. 8). ADP is subsequently added so as to induce ATP synthase function. Said ATP synthase will phosphorylate the ADP and, in doing so, it consumes the proton gradient, which is reflected by an increase in fluorescence. As the added ADP is phosphorylated, the potential increases once again (fewer and fewer protons are consumed by the ATP synthase) and the potential returns to the initial value when all the added ADP has been phosphorylated. For the MR14 mutant, the addition of ADP brings about only a very small decrease in potential, which returns very slowly to the value of the initial potential. This observation indicates a deficiency in the ATP synthase function. In order to define this deficiency more clearly, the energization of the mitochondrial membrane by ATP was analyzed. In this case, the ATP synthase was studied in reverse mode, i.e. when it hydrolyzes ATP. Normally, in hydrolyzing ATP, the ATP synthase evacuates protons out of the mitochondrion. In this operating mode, the ATP synthase therefore positively energizes the outside of the inner mitochondrial membrane. In the wild-type, immediately after the addition of ATP (in the presence of KCN to inhibit the respiratory chain), the establishment of a large and stable mitochondrial potential is noted. Subsequent addition of oligomycin (an inhibitor of the ATP synthase proton channel) leads, as expected, to the loss of this potential, thereby showing that the latter is indeed linked to the activity of the ATP synthase.

In the MR14 mutant, a decrease in fluorescence is also noted, immediately after the addition of ATP, but this decrease is smaller. Furthermore, there is a gradual return, without the addition of oligomycin, to the initial fluorescence value. The ATP synthase in the mutant is not therefore capable of correctly energizing the inner mitochondrial membrane. These observations show that the t8993g mutation is responsible for a major deficiency in ATP synthase function. A similar study carried out with the other mutants indicates that the t9176g mutation abolishes ATP synthase function, whereas the t8993c mutation indeed affects ATP synthase function, but to a much lesser extent than the t8993g mutation.

e) The t8993g Mutation does not Affect ATP Synthase Assembly and Stability

The effect of the t8993g mutation on the assembly or the stability of the ATP synthase complex was studied. Mitochondria from the wild-type (MR6) and mutant (MR14) strains were treated with digitonin at concentrations which make it possible to conserve the interactions inside the multiprotein complexes. The mitochondria were subsequently analyzed by nondenaturing gel electrophoresis (BN-PAGE technique). The results show that the ATP synthase complex is perfectly assembled and accumulates normally in the mutant (FIG. 9).

EXAMPLE 3

Screening for Molecules that Act Against Mitochondrial Pathologies Involving a Deficiency in Oxidative Phosphorylation, such as NARP Syndrome The t8993g, t9176g and t8851c mutants grow very slowly from a nonfermentable carbon source due to a dysfunction of the ATP synthase. These yeast mutants are therefore used to identify molecules capable of correcting the effects of the mutation by restoring either ATP synthase function, or ATP production by the mitochondria. The molecules capable of restoring ATP synthase function can potentially be used as a medicament for the treatment of NARP syndrome. The molecules capable of restoring ATP production by the mitochondria can potentially be used as a medicament for the treatment of mitochondrial pathologies involving a deficiency in ATP production via the oxidative phosphorylation pathway; these are pathologies related to a dysfunction of the mitochondrial energy system, such as, in particular, NARP syndrome, related to an ATP synthase dysfunction, and the syndromes LHON (Leber's Hereditary Ootic Neuropathy), MILS (Maternally Inherited Leigh Syndrome), MERRF (Myoclonic Epilepsy with Ragged-Red Fibers) and HSP (Hereditary Spastic Paraplegia), related to a respiratory complex dysfunction.

The principle of the screening test is described in Bach et al., Nature Biotechnology, 2003, 21, 1075-1081. More specifically, the screening is carried out according to the following steps (FIG. 10): Step 1: the mutant is cultured in medium containing glucose. Step 2: the mutant cells are plated out in a layer at the surface of an agar medium containing a nonfermentable carbon source such as glycerol. Step 3: filters which each contain a defined amount of one of the test molecules are placed on the Petri dish, the molecules diffuse in the medium and establish a concentration gradient around the filters. Step 4: the dishes are incubated. Under these conditions, a growth halo is seen to appear around the filters containing a substance capable of counteracting the effects of the mutation (drug C5).

EXAMPLE 4

Demonstration of Intragenic Suppressors of the t8993g Mutation

Intragenic suppressors of the t8993g mutation, i.e. mutations in the ATP6 gene which make it possible to restore sufficient ATP synthase function, were sought. For this, cells of the t8993g yeast mutant were plated out in a dense layer at the surface of a nutritive medium containing a nonfermentable carbon source (glycerol, N3 medium), i.e. conditions which do not allow the growth of the t8993g mutant. After a few days of incubation, revertant clones which have recovered a sufficient respiratory capacity emerge (FIG. 11). The ATP6 genes of the revertants where amplified by PCR and sequenced. This analysis revealed various intragenic suppressors (FIG. 11). Some were at the level of the codon modified by the t8993g mutation. These "first-site" suppressors result in the replacement of arginine 183 with an amino acid other than leucine present in the wild-type sequence of Atp6p, namely lysine, isoleucine or serine. These results show that the presence of a leucine in this position of the protein is not absolutely essential for ATP synthase function. In other revertants, the suppressor mutation was located in a codon other than that modified by the T8993G mutation. These "second-site" suppressors result in the replacement of arginine residue 179 with serine, of alanine residue 180 with proline or glycine, or of isoleucine residue 226 with serine (FIG. 11). It therefore appears that discrete changes in the Atp6p protein make it possible to compensate for the presence of an arginine at position 183.

These results indicate that small molecules capable of binding specifically to ATP synthase, in the vicinity of the Atp6p region modified by the t8993g mutation, could restore ATP synthase function by inducing a discrete conformational change which allows the constraint caused by the t8993g mutation to be relaxed. These molecules represent one of the potential pharmacological targets that can be used for the treatment of NARP syndrome. Such molecules may be selected by the screening assay described in example 3, using the t8993g, t9176g and t8851c yeast mutants which grow very slowly from a nonfermentable carbon source due to an ATP synthase dysfunction. The restoration of the ATP synthase function, by one of these molecules, is reflected by a restoration of the growth of the mutants, which can be readily detected in an agar medium.

EXAMPLE 5

Demonstration of Metabolic Suppressors of the t8993g Mutation

A mechanism of correction (by multicopy suppression) of a nuclear mutation causing a deficiency in ATP synthase assembly has been demonstrated (Schwimmer et al., J. Biol. Chem., 2005, 280, 30751-30759). This mutation (denoted Δfmc) is a null allele (complete deletion) of the nuclear FMC1 gene which encodes a mitochondrial matrix protein (Fmc1p) essential for assembly of sector $F_1$ of ATP synthase (Lefebvre-Legendre et al., J. Biol. Chem., 2001, 276, 6789-6796). The Δfmc1 mutant exhibits a strong respiratory growth deficiency at temperatures close to 37° C.; at 28° C., it grows normally, indicating that Fmc1p is necessary in a heat-sensitive step of ATP synthase assembly. The respiratory growth of the Δfmc1 mutant is restored by overexpression of Odc1p in the cells, through an increase in the number of copies to its gene (Schwimmer et al., 2005, mentioned above). The Odc1p protein is a dicarboxylate (α-ketoglutarate and α-ketoadipate) transporter located in the inner mitochondrial membrane (Palmieri et al., J. Biol., Chem., 2001, 276, 1916-1922). In the Δfmc1 strain overexpressing Odc1p, the deficiency in ATP synthase due to the inactivation of FMC1 is still present. The increase in dicarboxylate flux between the cytosol and the mitochondrial matrix following overexpression of Odc1p allows a greater intramitochondrial production of ATP via ADP phosphorylations coupled to the Krebs-cycle reaction of oxidative decarboxylation of α-keto-glutarate ("substrate-level phosphorylation", FIG. 12). It is therefore a mechanism of metabolic suppression, which acts by bypassing the ATP synthase deficiency in the Δfmc1 mutant.

The effect of the overexpression of Odcp1 on the deficiency in ATP synthase function caused by the t8893g mutation was analyzed, in vitro and in vivo.

The wild-type strain (MR6), the t8993g mutant strain (MR14) and the t8993g mutant strain overexpressing Odc1p (MR14/ODC1) were cultured overnight in a medium containing glucose (YPGA). The cultures were serially diluted and a drop of each dilution was deposited onto YPGA medium and a medium containing glycerol as carbon source (N3). The dishes were subsequently incubated at 36° C. and then photographed after incubation for 7 days (FIG. 12). In vivo, the improvement in respiratory growth is much less effective than in the case of the Δfmc1 mutant, and is really only significant at temperatures close to 37° C. (FIG. 12). The analysis of the proteins extracted from the MR6, MR14 and MR14/ODC1 strains, by Western blotting with antibodies directed against Odc1p, confirms that Odcp1 is overexpressed in the MR14/ODC1 strain (FIG. 12).

The mitochondria were isolated from the wild-type strain (MR6), the t8993g mutant strain (MR14) and the t8993g mutant strain overexpressing Odc1p (NARP 2m ODC) cultured in YPGAL at 37° C., in the presence of the following substances: 0.15 mg/ml of proteins, 4 mM NADH (state 4), 400 μM ADP (state 3), 6 μg/ml of oligomycin, 3 μM CCCP, 15 mM ascorbate (Asc), 1.4 mM TMPD, 5 mM α-ketoglutarate (α-KG) (tables II & III).

In vitro, the mitochondria isolated from the t8993g mutant strain overexpressing Odc1p have an ATP synthase activity close to that measured with the mitochondria of the corresponding wild-type strain, when α-ketoglutarate is used as respiratory substrate (table III).

TABLE II

Respiratory chain activity and ATP synthase complex activity on NADH

| | | Oxygen consumption rate (nAt/min/mg) | | | | Synthesis of ATP on NADH | | |
|---|---|---|---|---|---|---|---|---|
| | | NADH | | | Asc/TMPD | (pmol/min/mg) | | |
| Strain | % ρ⁻/ρ°* | State 4 | State 3 | +CCCP | +CCCP | −oligo | +oligo | Comp. V |
| WT | 27 ± 1 | 93 ± 4.5 | 287 ± 7 | 596 ± 2 | 886 ± 15 | 383 ± 15 | 95 ± 8 | 288 ± 10 |
| NARP | 24 ± 0 | 50 ± 9 | 50 ± 9 | 95 ± 13 | 132 ± 16 | 39 ± 6 | 8 ± 2 | 30 ± 4 |
| NARP 2m ODC | 19 ± 1 | 45 ± 0.2 | 109 ± 0.5 | 254 ± 5 | 378 ± 12 | 74 ± 12 | 7 ± 1 | 67 ± 11 |

*The percentages of small ρ⁻/ρ° in the cultures are indicated.

TABLE III

Respiratory chain activity and ATP synthase complex activity on α-ketoglutarate

| | | Oxygen consumption α-KG | | ATP synthesis on α-KG (pmol/min/mg) | | |
|---|---|---|---|---|---|---|
| Strain | % ρ⁻/ρ°* | −ADP | +ADP | −oligo | +oligo | Comp. V |
| WT | 27 ± 1, | 22 | 125 ± 1.5 | 200 ± 3 | 71 ± 2 | 132 ± 3 |
| NARP | 24 ± 0 | 25 ± 2 | 28 ± 5 | 43 ± 5 | 17 ± 1 | 27 ± 3 |
| NARP 2m ODC | 19 ± 1 | 20 ± 0.4 | 91 ± 1 | 166 ± 1 | 49 ± 4 | 117 ± 3 |

*The percentages of small ρ⁻/ρ° in the cultures are indicated.

The results clearly show two distinct beneficial effects of the overexpression of Odc1p: (i) the respiratory complexes, especially complex IV, further accumulate, and (ii) the fraction of ATP production by a substrate-level ADP phosphorylation significantly increases.

These data show that it is possible to compensate for a mutation which inactivates ATP synthase, such as the t8993g mutation, via a mechanism which does not restore ATP synthase function, but acts by stimulating another mitochondrial source of ATP production, namely the reaction of oxidative decarboxylation of α-ketoglutarate which is coupled to ADP phosphorylation. Such a mechanism could also compensate for deficiencies in oxidative phosphorylation due to mutations affecting enzymes other than ATP synthase, in particular the respiratory complexes. The latter are often involved in pathologies, such as LHON (Leber's Hereditary Ootic Neuropathy), MILS (Maternally Inherited Leigh Syndrome), MERRF (Myoclonic Epilepsy with Ragged-Red Fibers) or HSP (Hereditary Spastic Paraplegia). Thus, a molecule capable of bypassing the t8993g mutation via a mechanism such as that demonstrated above could also act against other pathologies associated with mutations that impair ATP production via the oxidative phosphorylation pathway.

The invention claimed is:

1. An isolated genetically-modified *Saccharomyces cerevisiae* yeast strain comprising at least one mutation in the mitochondrial ATP6 gene selected from the group consisting of:
- a tryptophan to arginine substitution at codon 136 (W136R),
- a leucine to arginine substitution at codon 183 (L183R),
- a leucine to arginine substitution at codon 247 (L247R),
- a leucine to proline substitution at codon 183 (L183P), and
- a leucine to proline substitution at codon 247 (L247P),
- wherein said codon(s) correspond to that/those of the mitochondrial ATP6 gene consisting of the nucleotide sequence SEQ ID NO: 1.

2. The yeast strain of claim 1, which comprises a mutation that is W136R.

3. The yeast strain of claim 1, which comprises a mutation that is L183R.

4. The yeast strain of claim 1, which comprises a mutation that is L247R.

5. The yeast strain of claim 1, which comprises a mutation selected from the group consisting of L183P and L247P.

6. The yeast strain of claim 1, which is a rho$^+$ strain of *Saccharomyces cerevisiae.*

7. A method of screening for candidate molecules that can be used for the treatment of NARP syndrome, comprising:
- a) culturing the yeast strain of claim 1, which comprises at least one mutation selected from the group consisting of W136R, L183R, and L247R, in the presence of a test molecule, in a medium containing a nonfermentable carbon source, and
- b) identifying the candidate molecules consisting of the test molecules capable of restoring the growth of said yeast strain.

8. The method of claim 7, wherein said yeast strain is a rho$^+$ strain of *Saccharomyces cerevisiae.*

9. The method as claimed in claim 7, wherein said culture medium in step a) is an agar medium.

10. The method as claimed in claim 7, wherein said nonfermentable carbon source is selected from the group consisting of: glycerol, ethanol and lactate.

11. A method of screening for candidate molecules capable of correcting *Saccharomyces cerevisiae* ATP synthase dysfunction caused by the W136R, L183R, and/or L247R mutation in mitochondrial ATP6 gene, comprising:
- a) culturing the yeast strain of claim 1, which comprises at least one mutation selected from the group consisting of W136R, L183R, and L247R, in the presence of a test molecule, in a medium containing a nonfermentable carbon source, and
- b) identifying the candidate molecules consisting of the test molecules capable of restoring the growth of said yeast strain.

12. The method of claim 11, wherein said candidate molecule is a metabolic suppressor of the ATP6 gene mutation.

13. The method of claim 11, wherein said test molecule is a small molecule capable of binding specifically to ATP synthase.

14. The method of claim 11, wherein said culture medium in step a) is an agar medium.

15. The method of claim 11, wherein said nonfermentable carbon source is selected from the group consisting of: glycerol, ethanol and lactate.

16. The method of claim 11, wherein said yeast strain is a $rho^+$ strain of *Saccharomyces cerevisiae*.

* * * * *

SEQUENCE LISTING

<160> NUMBER OF SEQ ID NOS: 16

<210> SEQ ID NO 1
<211> LENGTH: 780
<212> TYPE: DNA
<213> ORGANISM: Saccharomyces cerevisiae

<400> SEQUENCE: 1

```
atgtttaatt tattaaatac atatattaca tcaccattag atcaatttga gattagacta     60

ttatttggtt tacaatcatc atttattgat ttaagttgtt taaatttaac aacattttca    120

ttatatacta ttattgtatt attagttatt acaagtttat atctattaac taataataat    180

aataaaatta ttggttcaag atgattaatt tcacaagaag ctatttatga tactattata    240

aatatgctta aaggacaaat tggaggtaaa aattgaggtt tatatttccc tatgatcttt    300

acattattta tgtttatttt tattgctaat ttaattagta tgattccata ctcatttgca    360

ttatcagctc atttagtatt tattatctct ttaagtattg ttatttgatt aggtaatact    420

attttaggtt tatataaaca tggttgagta ttcttctcat tattcgtacc tgctggtaca    480

ccattaccat tagtaccttt attagttatt attgaaactt tatcttattt cgctagagct    540

atttcattag gtttaagatt aggttctaat atcttagctg gtcatttatt aatggttatt    600

ttagctggtt tactatttaa ttttatgtta attaatttat ttactttagt attcggtttt    660

gtacctttag ctatgatctt agccattatg atgttagaat tcgctattgg tatcattcag    720

ggatatgtct gggctatttt aacagcatca tatttaaaag atgcagtata cttacattaa    780
```

<210> SEQ ID NO 2
<211> LENGTH: 259
<212> TYPE: PRT
<213> ORGANISM: Saccharomyces cerevisiae

<400> SEQUENCE: 2

```
Met Phe Asn Leu Leu Asn Thr Tyr Ile Thr Ser Pro Leu Asp Gln Phe
1               5                   10                  15

Glu Ile Arg Thr Leu Phe Gly Leu Gln Ser Ser Phe Ile Asp Leu Ser
            20                  25                  30

Cys Leu Asn Leu Thr Thr Phe Ser Leu Tyr Thr Ile Ile Val Leu Leu
        35                  40                  45

Val Ile Thr Ser Leu Tyr Thr Leu Thr Asn Asn Asn Asn Lys Ile Ile
    50                  55                  60

Gly Ser Arg Trp Leu Ile Ser Gln Glu Ala Ile Tyr Asp Thr Ile Met
65                  70                  75                  80

Asn Met Thr Lys Gly Gln Ile Gly Gly Lys Asn Trp Gly Leu Tyr Phe
                85                  90                  95

Pro Met Ile Phe Thr Leu Phe Met Phe Ile Phe Ile Ala Asn Leu Ile
            100                 105                 110

Ser Met Ile Pro Tyr Ser Phe Ala Leu Ser Ala His Leu Val Phe Ile
        115                 120                 125

Ile Ser Leu Ser Ile Val Ile Trp Leu Gly Asn Thr Ile Leu Gly Leu
    130                 135                 140

Tyr Lys His Gly Trp Val Phe Phe Ser Leu Phe Val Pro Ala Gly Thr
145                 150                 155                 160

Pro Leu Pro Leu Val Pro Leu Leu Val Ile Ile Glu Thr Leu Ser Tyr
                165                 170                 175

Phe Ala Arg Ala Ile Ser Leu Gly Leu Arg Leu Gly Ser Asn Ile Leu
```

```
            180                 185                 190

Ala Gly His Leu Leu Met Val Ile Leu Ala Gly Leu Thr Phe Asn Phe
        195                 200                 205

Met Leu Ile Asn Leu Phe Thr Leu Val Phe Gly Phe Val Pro Leu Ala
    210                 215                 220

Met Ile Leu Ala Ile Met Met Leu Glu Phe Ala Ile Gly Ile Ile Gln
225                 230                 235                 240

Gly Tyr Val Trp Ala Ile Leu Thr Ala Ser Tyr Leu Lys Asp Ala Val
                245                 250                 255

Tyr Leu His


<210> SEQ ID NO 3
<211> LENGTH: 88
<212> TYPE: DNA
<213> ORGANISM: Artificial sequence
<220> FEATURE:
<223> OTHER INFORMATION: Description of Artificial Sequence: Synthetic
      primer

<400> SEQUENCE: 3

gcgggatcct ttattatagt ttaatactcc atatgtaaat tattttattt tataatttta     60

ttttataatt taagcatata cagcttcg                                         88


<210> SEQ ID NO 4
<211> LENGTH: 88
<212> TYPE: DNA
<213> ORGANISM: Artificial sequence
<220> FEATURE:
<223> OTHER INFORMATION: Description of Artificial Sequence: Synthetic
      primer

<400> SEQUENCE: 4

gcctagataa taagatataa ttatgattaa ttattataag ttatatagtt ttataaattt     60

ataattatta tgacacattt agaaagaa                                         88


<210> SEQ ID NO 5
<211> LENGTH: 19
<212> TYPE: DNA
<213> ORGANISM: Artificial sequence
<220> FEATURE:
<223> OTHER INFORMATION: Description of Artificial Sequence: Synthetic
      primer

<400> SEQUENCE: 5

gcggacccca aaggaggag                                                   19


<210> SEQ ID NO 6
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 6

cgggatccca gtggggaagg agtgaggt                                         28


<210> SEQ ID NO 7
<211> LENGTH: 19
<212> TYPE: PRT
<213> ORGANISM: Saccharomyces cerevisiae

<400> SEQUENCE: 7
```

```
Ala Ile Ser Leu Gly Leu Arg Leu Gly Ser Asn Ile Leu Ala Gly His
1               5                   10                  15

Leu Leu Met


<210> SEQ ID NO 8
<211> LENGTH: 19
<212> TYPE: PRT
<213> ORGANISM: Escherichia coli

<400> SEQUENCE: 8

Pro Val Ser Leu Gly Leu Arg Leu Phe Gly Asn Met Tyr Ala Gly Glu
1               5                   10                  15

Leu Ile Phe


<210> SEQ ID NO 9
<211> LENGTH: 19
<212> TYPE: PRT
<213> ORGANISM: Homo sapiens

<400> SEQUENCE: 9

Pro Met Ala Leu Ala Val Arg Leu Thr Ala Asn Ile Thr Ala Gly His
1               5                   10                  15

Ile Leu Met


<210> SEQ ID NO 10
<211> LENGTH: 19
<212> TYPE: PRT
<213> ORGANISM: Podospora anserina

<400> SEQUENCE: 10

Asn Ile Ser Leu Gly Leu Arg Leu Ala Ala Asn Ile Leu Ser Gly His
1               5                   10                  15

Met Leu Leu


<210> SEQ ID NO 11
<211> LENGTH: 19
<212> TYPE: PRT
<213> ORGANISM: Aspergillus nidulans

<400> SEQUENCE: 11

Asn Val Ser Leu Gly Leu Arg Leu Ala Ala Asn Ile Leu Ser Gly His
1               5                   10                  15

Met Leu Leu


<210> SEQ ID NO 12
<211> LENGTH: 19
<212> TYPE: PRT
<213> ORGANISM: Neurospora crassa

<400> SEQUENCE: 12

Asn Ile Ser Leu Gly Leu Arg Leu Ala Ala Asn Ile Leu Ser Gly His
1               5                   10                  15

Met Leu Leu


<210> SEQ ID NO 13
<211> LENGTH: 19
<212> TYPE: PRT
<213> ORGANISM: Drosophila sp.

<400> SEQUENCE: 13

Pro Gly Thr Leu Ala Val Arg Leu Thr Ala Asn Met Ile Ala Gly His
1               5                   10                  15
```

```
Leu Leu Leu


<210> SEQ ID NO 14
<211> LENGTH: 19
<212> TYPE: PRT
<213> ORGANISM: Xenopus laevis

<400> SEQUENCE: 14

Pro Leu Ala Leu Gly Val Arg Leu Thr Ala Asn Leu Thr Ala Gly His
1               5                   10                  15

Leu Leu Ile


<210> SEQ ID NO 15
<211> LENGTH: 19
<212> TYPE: PRT
<213> ORGANISM: Rattus sp.

<400> SEQUENCE: 15

Pro Met Ala Leu Ala Val Arg Leu Thr Ala Asn Ile Thr Ala Gly His
1               5                   10                  15

Leu Leu Met


<210> SEQ ID NO 16
<211> LENGTH: 19
<212> TYPE: PRT
<213> ORGANISM: Bos sp.

<400> SEQUENCE: 16

Pro Met Ala Leu Ala Val Arg Leu Thr Ala Asn Ile Thr Ala Gly His
1               5                   10                  15

Leu Leu Ile
```